(12) United States Patent
Berkland et al.

(10) Patent No.: US 7,993,749 B2
(45) Date of Patent: Aug. 9, 2011

(54) NANOPARTICLES COMPRISING A NANOPARTICLE TEMPLATE AND A POLYMER SHELL HAVING AN AMIDE SIDE CHAIN, AND METHOD OF MAKING THEREOF

(75) Inventors: Cory J. Berkland, Lawrence, KS (US); Lianjun Shi, Bridgewater, NJ (US)

(73) Assignee: University of Kansas, Lawrence, KS (US)

( * ) Notice: Subject to any disclaimer, the term of this patent is extended or adjusted under 35 U.S.C. 154(b) by 673 days.

(21) Appl. No.: 11/893,846

(22) Filed: Aug. 17, 2007

(65) Prior Publication Data

US 2008/0075667 A1  Mar. 27, 2008

Related U.S. Application Data

(63) Continuation-in-part of application No. 11/610,986, filed on Dec. 14, 2006, now Pat. No. 7,651,770.

(60) Provisional application No. 60/751,172, filed on Dec. 16, 2005.

(51) Int. Cl.
*B32B 5/16* (2006.01)
*C08F 2/10* (2006.01)

(52) U.S. Cl. ........ 428/407; 427/212; 427/215; 427/221; 427/487; 524/173; 524/174; 524/812

(58) Field of Classification Search .................. 428/403, 428/407; 524/173, 174, 812; 427/212, 215, 427/221, 487
See application file for complete search history.

(56) References Cited

U.S. PATENT DOCUMENTS

| | | | |
|---|---|---|---|
| 5,358,702 A | 10/1994 | Unger | |
| 5,470,903 A * | 11/1995 | Lenney et al. | 524/458 |
| 5,976,783 A * | 11/1999 | Powell et al. | 435/4 |
| 6,602,932 B2 | 8/2003 | Feldheim et al. | |
| 6,669,961 B2 | 12/2003 | Kim et al. | |
| 7,056,901 B2 * | 6/2006 | Frechet et al. | 514/54 |
| 7,129,293 B2 * | 10/2006 | Kataoka et al. | 525/69 |
| 2003/0138490 A1 | 7/2003 | Hu et al. | |
| 2003/0211158 A1 | 11/2003 | Frechet et al. | |
| 2005/0019270 A1 | 1/2005 | Finlay et al. | |
| 2005/0053667 A1 | 3/2005 | Irvine et al. | |
| 2006/0223776 A1 | 10/2006 | Frechet et al. | |

FOREIGN PATENT DOCUMENTS

| | | |
|---|---|---|
| WO | WO 03/022910 | 3/2003 |
| WO | WO 03/100034 | 12/2003 |

OTHER PUBLICATIONS

Fleming et al., Nanosphere-microsphere Assembly: Methods for core-shell materials preparation, Chem. Mater. 2001, 13, 2006 2210-2216.*

(Continued)

*Primary Examiner* — H. (Holly) T Le
(74) *Attorney, Agent, or Firm* — Baker Botts L.L.P.

(57) ABSTRACT

Acid-labile poly(N-vinyl formamide) ("PNVF") nanocapsules were synthesized by free radical polymerization of N-vinyl formamide with optional active ingredients on the surface of silica nanoparticles. Polymerization in the presence of a novel cross-linker that contains an acid-labile ketal facilitated stable etching of silica nanoparticle templates using sodium hydroxide and recovery of PNVF nanocapsules. The formamido side group of PNVF was then hydrolyzed by extended exposure to sodium hydroxide to produce polyvinylamine ("PVAm") nanocapsules. PNVF and PVAm nanoparticles are also synthesized that form nanogels with optional active ingredients.

22 Claims, 17 Drawing Sheets

OTHER PUBLICATIONS

Uyama et al., *Dispersion Polymerization of N-Vinylformamide in Polar Media. Preparation of Monodisperse Hydrophilic Polymer Particles*, Polymer Journal 26:7 858-863 (1994).

Shi et al., *pH-Triggered Dispersion of Nanoparticle Clusters*, Adv. Mater. 18 2315-2319 (2006) Published on-line Aug. 28, 2006.

Adjei et al., *Pulmonary delivery of peptide drugs: effect of particle size on bioavailability of leuprolide acetate in healthy male volunteers*, Pharm. Res., 7:565-569 (1990).

"American Lung Association State of the Air: 2006," American Lung Association, (2006).

Anderson, *Delivery options and devices for aerosolized therapeutics*, Chest, 120 89S-93S (2001).

Berkland et al., *Fabrication of PLG microspheres with precisely controlled and monodisperse size distributions*, J. Control Release, 73 59-74 (2001).

Berkland et al., *Precise control of PLG microsphere size provides enhanced control of drug release rate*, J. Control Release, 82 137-47 (2002).

Berkland et al., *Uniform double-walled polymer microspheres of controllable shell thickness*, J. Control Release, 96 101-111 (2004).

Berkland et al., *Precision polymer microparticles for controlled-release drug delivery*, ACS Sym. Ser. (2002).

Berkland, *Control of micro- and nano-sphere size distributions: implications in drug delivery*, Chemical Engineering, Urbana-Champaign, University of Illinois, pp. 78 (2001).

Grenha et al., *Microencapsulated chitosan nanoparticles for lung protein delivery*, Eur. J. Pharm. Sci., 25 427-437 (2005).

Griesenbach et al., *Advances in cystic fibrosis gene therapy*, Curr. Opin. Pulm. Med., 10(6) 542-546 (2004).

John et al., *Discovery of potent nanoparticle P-selectin antagonist with anti-inflammatory effects in allergic airway disease*, Faseb. J., 17(15) 2296-2298 (2003).

Johnson et al., *Delivery of albuterol and ipratropium bromide from two nebulizer systems in chronic stable asthma: efficacy and pulmonary deposition*, Chest, 96(1) 6-10 (1989).

Kim et al., *Assessment of regional deposition of inhaled particles in human lungs by serial bolus delivery method*, J. Appl. Physiol. 81 2203-2213 (1996).

Kumar et al., *Chitosan IFN-γ-pDNA nanoparticle (CIN) therapy for allergic asthma*, Genet. Vaccines Ther., 1(1) 3 (2003).

Labiris et al., *Pulmonary drug delivery. Part I: physiological factors affecting therapeutic effectiveness of aerosolized medications*, Br. J. Clin. Pharmacol. 56 588-599 (2003).

Lindgren et al., *Clinical consequences of inadequate inhalation technique in asthma therapy*, Eur. J. Respir. Dis. 70 93-98 (1987).

Mainardes et al., *Microcapsules, liposomes, nanoparticles, microcells, microspheres*, J Microencapsul. 22 13-24 (2005).

Manoharan et al., *Dense Packing and Symmetry in Small Clusters of Microspheres*, Science 301 483-487 (2003).

Marier et al., *Liposomal tobramycin against pulmonary infections of Pseudomonas aeruginosa: a pharmacokinetic and efficacy study following single and multiple intratracheal administrations in rats*, J. Antimicrob. Chemother. 52 247-252 (2003).

Musante et al., *Factors affecting the deposition of inhaled porous drug particles*, J. Pharm. Sci, 91 1590-1600 (2002).

Newman et al., *Scintigraphic comparison of budesonide deposition from two dry powder inhalers*, Eur. Respir. J. 16 178-183 (2000).

Newman, *Drug Delivery to the lungs from dry powder inhalers*, Curr. Opin. Pulm. Med. 9 S17-S20 (2003).

Niven, *Delivery of biotherapeutics by inhalation aerosol*, Crit. Rev. Ther. Drug Carrier Syst. 12 151-231 (1995).

Patton et al., *Pulmonary delivery of peptides and proteins for systemic action*, Advanced Drug Delivery Reviews 8 179-196 (1992).

Patton, *Deep lung delivery of therapeutic proteins*, CHEMTECH 27 34-38 (1997).

Pritchard, *The influence of lung deposition on clinical response*, J. Aerosol Med. 14 S19-S26 (2001).

Rasenack et al., *Micron-size drug particles: common and novel micronization techniques*, Pharm. Dev. Technol. 9 1-13 (2004).

Reed et al., *Aerosol beclomethasone dipropionate spray compared with theophylline as primary treatment for chronic mild-to-moderate asthma*, J. Allergy Clin. Immunol. 101 14-23 (1998).

Schuepp et al., *Deposition of aerosols in infants and children*, J. Aerosol. Med. 17 153-156 (2004).

Scott et al., *Enhanced gene delivery to human airway epithelial cells using an intergrin-targeting lipoplex*, J. Gene Med. 3 125-134 (2001).

Sham et al., *Formulation and characterization of spray-dried powders containing nanoparticles for aerosol delivery to the lung*, Int. J. Pharm. 269(2) 457-467 (2004).

St. John et al., *Hydrogel Nanoparticle Aggregates*, PowerPoint Presentation, Access Pharmaceuticals Inc., 113.

Surendrakumar et al., *Sustained release of insulin from sodium hyaluronate based dry powder formulations after pulmonary delivery to beagle dogs*, J. Control Release 91 385-394 (2003).

Tsapis, *Trojan particles: large porous carriers of nanoparticles for drug delivery*, Proc. Natl. Acad. Sci. USA 99 12001-12005 (2002).

Wittaya-Areekul et al., *Freeze-drying of tert-Butanol/water cosolvent systems: a case report on formation of a friable freeze-dried powder of tobramycin sulfate*, J. Pharm. Sci. 91 1147-1155 (2002).

Yi et al., *Colloidal clusters of silica or polymer microspheres*, Adv. Mater. 16 1204-1208 (2004).

Yoshizawa et al., *Immune responsiveness to inhaled antigens: local antibody production in the respiratory tract in health and lung diseases*, Clin. Exp. Immunol. 100 395-400 (1995).

\* cited by examiner a: p-toluenesulfonic acid, benzene; b: THF, ice bath; c: dicyclohexyl-18-crown-6, room temperature

US 7,993,749 B2

NANOPARTICLES COMPRISING A NANOPARTICLE TEMPLATE AND A POLYMER SHELL HAVING AN AMIDE SIDE CHAIN, AND METHOD OF MAKING THEREOF

CROSS-REFERENCE TO RELATED APPLICATIONS

This application claims priority to and is a continuation-in-part application of U.S. patent application Ser. No. 11/610,986, now U.S. Pat. No. 7,651,770 filed on Dec. 14, 2006, which claims priority to U.S. provisional patent application Ser. No. 60/751,172 filed on Dec. 16, 2005, both of which are incorporated herein by reference.

STATEMENT REGARDING FEDERALLY SPONSORED RESEARCH OR DEVELOPMENT

Not applicable.

FIELD OF THE INVENTION

The present invention pertains generally to novel nanoparticles, nanogels, composite nanoparticles, and hollow nanocapsules and to methods for synthesizing the same.

BACKGROUND OF THE INVENTION

Various hydrogels have been investigated as a potential approach for the delivery of various active ingredients, especially pharmaceutical and other bioactive materials. For example, microgels and microparticles made of acrylamides and methacrylamides formed using an aryl cross-linker capable of delivering bioactive materials to cells have been described in Frechet et al., U.S. Pat. No. 7,056,901, which is incorporated by reference. In many instances, it is preferable that the hydrogels release their contents in response to an environmental stimuli, allowing for the targeting of protein therapeutics to diseased tissues and cells. A particularly important environmental stimulus is mildly acidic pH. For example, tumors exist at acidic pHs between 6.4 to 6.8, and the phagolysosomes of phagocytic cells are at pHs between about 4.5 to 5.0. The acidic nature of these compartments has stimulated a need for the development of hydrogels that can selectively release their contents under mildly acidic conditions.

In addition, hollow particles, also referred to as capsules or vesicles, are generating interest in industry, as well as scientific research. For example, Feldheim et al., U.S. Pat. No. 6,602,932, which is incorporated by reference, describes polypyrrole nanoparticle composites and nanocapsules which encapsulate a "guest molecule."

While there has been significant progress, there remains a need to develop additional novel nanoparticles, nanogels, composite nanoparticles, and nanocapsules useful in the delivery of various active ingredients.

BRIEF SUMMARY OF THE INVENTION

The present invention is directed to novel pH-insensitive and pH-sensitive nanoparticles, nanogels, composite nanoparticles, and hollow nanocapsules. In one aspect, the present invention is directed to a composition of matter comprising polyvinyl formamide ("PNVF") nanoparticles or nanogels, which may be partially or fully hydrolyzed to form polyvinyl amine ("PVAm") nanoparticles or nanogels. In another aspect, the present invention is directed to a composition of matter comprising silica nanoparticles coated with a PNVF shell to form PNVF-coated silica composite nanoparticles. The PNVF may be fully or partially hydrolyzed to form PVAm-coated silica composite nanoparticles. In another aspect, the PNVF-coated silica composite nanoparticles are subjected to silica etching at a high pH to form hollow PNVF nanocapsules. In a further aspect, the PNVF nanocapsules may be further processed by hydrolysis of the formamido side group to generate PVAm nanocapsules.

In another aspect, the nanoparticles, nanogels, composite nanoparticles, and nanocapsules further comprise an active ingredient associated therewith. Non-limiting examples of active ingredients that are contemplated as being useful in the context of the present invention include those known to a person of ordinary skill and those described throughout this specification. By way of example only, active ingredients can include medical pharmaceuticals and specialties such as preventive agents, for example, vaccines, diagnostic agents, for example, tracers of various types and imaging enhancers, therapeutic agents, for example, small molecules, nucleic acids, drugs, peptides, polypeptides, proteins, and radiation, immuno-modulators, vaccine and virus vectors, and combinations of these classes. In particular embodiments, the active ingredient includes respirable non-medical specialties, such as physiochemical agents, for example gas antidotes, biophysical modulators, for example, paramagnetics, emitters, for example, electromagnetic wave emitters, and imaging enhancers.

In another aspect, the present invention is directed to methods for synthesizing the nanoparticles, composite nanoparticles, and hollow nanocapsules. For example, in an exemplary aspect, the nanoparticles (in the form of solid nanogels) may be formed with an optional active ingredient using inverse emulsion polymerization. The nanoparticles may be sonicated in order to control the particle size. The composite nanoparticles may be formed by polymerizing a monomer on the nanoparticle template to form a composite nanoparticle comprising the shell and the nanoparticle template. The hollow nanoparticles may then be formed by partially or fully removing the template, for example using a suitable etchant.

In a further aspect, the method comprises: providing a nanoparticle template; and forming PNVF shell on the nanoparticle template by polymerizing an NVF monomer on the nanoparticle template to form a composite nanoparticle comprising the PNVF shell and the nanoparticle template.

In still a further aspect, a method for synthesizing hollow nanocapsules is also provided. The method comprises: providing a nanoparticle template; forming a PNVF shell on the nanoparticle template by polymerizing a N-vinyl formamide ("NVF") monomer on the nanoparticle template; and at least partially dissolving the nanoparticle template to form a hollow nanocapsule defined by the shell.

In addition, methods for associating an active ingredient with the nanoparticles, composite nanoparticles, and nanocapsules are also provided. In an exemplary aspect, the method comprises providing a nanoparticle template conjugated to the active ingredient; and forming a PNVF shell on the nanoparticle template by polymerizing a monomer on the nanoparticle template to thereby encapsulate the active ingredient. In another aspect, the method further comprises dissolving the nanoparticle template to form a nanocapsule defined by the capsule shell material, wherein the active ingredient resides at least partially within the nanocapsule.

In another aspect, the monomers may be mixed with the cross-linker, initiator, and active ingredient (e.g., enzymes such as lysozyme) and then polymerized to form a nanogel encapsulated by the active ingredient.

In another aspect, the nanogels, such as the positive-charged PVAm nanogels may be mixed with negatively charged active ingredients, such nucleic acids (e.g., DNA, RNA, and the like) to form a complex.

In still another aspect, the nanogels may be mixed with suitable coupling agents and the active ingredient. Preferred coupling agents are succinimides and carbodiimides, such as those involving N-hydroxysucciimide ("NHS") and 1-ethyl-3-(3-dimethyl-aminopropyl) carbodiimide hydrochloride ("EDC").

In one aspect, the resulting nanoparticles, composite nanoparticles, and hollow nanocapsules possess colloidal stability in a variety of media such as water, ethanol, and toluene. These materials are well adapted to form nanogels.

In another aspect, the shell thickness of the composite nanoparticles and nanocapsules may be modulated by controlling the monomer concentration, reaction rate, temperature, and duration of free radical polymerization.

In yet another aspect, nanoparticles, nanogels, composite nanoparticles, and nanocapsules are provided in which the conversion of PNVF to PVAm ranges between 0 and 100%. In another aspect, the conversion of PNVF to PVAm about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100%.

In still another aspect the present invention is directed to a novel, acid-labile cross-linker. The acid-labile cross-linker is used for the polymerization of NVF to form the PNVF nanoparticles, composite nanoparticles, and nanocapsules of the present invention. In one aspect, the cross-linker is defined according to Formula I:

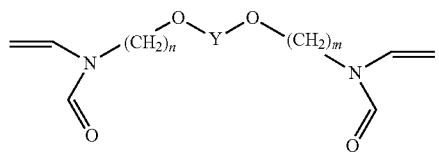

wherein n and m are independently an integer of between 1 and 10; and
wherein Y is a lower alkyl.

In a further aspect, the acid-labile cross-linker is defined according to Formula II:

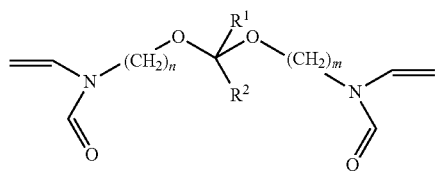

wherein n and m are independently an integer of between 1 and 10; and
wherein $R^1$ and $R^2$ are independently a lower alkyl, preferably methyl.

In a preferred aspect, the acid-labile cross-linker is 2-bis[2,2'-di(N-vinylformamido)ethoxy]propane ("BDEP").

In still another aspect the present invention is directed to a novel acid-stable (non-degradable) cross-linker. The cross-linker is used for the polymerization of NVF to form the PNVF nanoparticles, composite nanoparticles, and nanocapsules of the present invention. In one aspect, the cross-linker is defined according to Formula III:

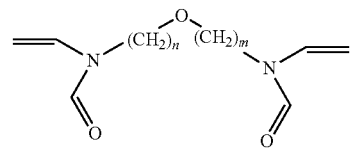

wherein n and m are independently an integer of between 1 and 10.

In a preferred aspect, the acid-stable cross-linker 2-(N-vinylformamido)ethyl ether.

In yet another aspect, the present invention is directed to a nanoparticles, nanogels, composite nanoparticles, and nanocapsules which demonstrate increasingly rapid degradation as pH is decreased.

In a further aspect, the PNVF and PVAm nanocapsules and solid PNVF and PVAm nanogels exhibit increased swelling as pH is decreased dependent on the degree of amino conversion. The magnitude of swelling correlates with an increase in zeta potential of the nanosuspension as the pH is lowered. Presumably, the increased number (amino conversion) and/or charging (pH) of the protonated amino groups results in a stretching of the crosslinked polymer network.

In another aspect, the synthesis methods of the present invention provide a unique approach to generate nanocapsules with multiple desirable properties including the size of the capsules (and thickness), pH responsiveness, biodegradability, and surface functionality.

From an applied perspective, the nanoparticles, nanogels, composite nanoparticles and nanocapsules of the present invention provide tremendous advances in such areas as nanoscale electronics, optics, environmental waste removal, drug delivery, biotechnology, and gene therapy.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 7 shows that the degradation of PVAm nanocapsules over time is strongly dependent upon the media pH.

FIG. 8 shows the optical density of nanocapsule suspensions as a function of time.

FIG. 13A generally shows the inverse emulsion process, followed by purification, usually one or more centrifuging cycles to isolate the nanoparticles. FIG. 13B shows how proteins, polypeptides, and other active incrediates may be loaded onto the nanogels. It will be appreciated that the PNVF nanogel can be readily converted to a PVAm nanogel.

DETAILED DESCRIPTION OF PREFERRED EMBODIMENT

Figure 1:
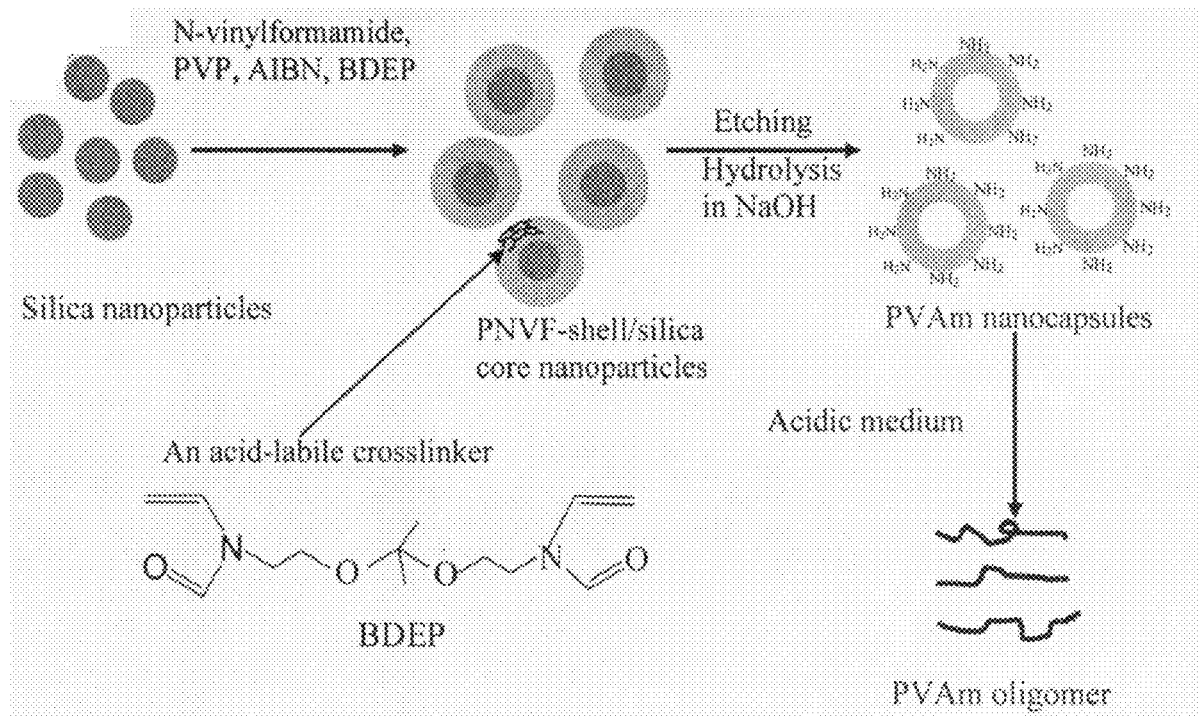
FIG. 1 is a schematic representation of the process for the preparation of PNVF-coated composite nanoparticles and PVAm nanocapsules. Silica nanoparticles are coated with a PNVF shell, and the etched to form PVAm nanocapsules.

The present invention is directed to novel nanoparticles, nanogels, composite nanoparticles and novel hollow nanocapsules associated with an optional active ingredient. In an exemplary aspect, the present invention is directed to acid-labile partially or fully hydrolyzed PNVF or PVAm nanoparticles that form a nanogel. In another exemplary aspect, the present invention is directed to a composite nanoparticle comprising a PNVF shell formed on a silica nanoparticle template by free-radical polymerization of NVF and crosslinking the PNVF using a novel cross-linker, 2-bis[2,2'-di(N-vinylformamido)ethoxy]propane ("BDEP"), which contains an acid-labile ketal. The silica nanoparticle template may be removed by etching to form hollow nanocapsules of PNVF. In addition, the PNVF shell may be partially or fully hydrolyzed to form PVAm composite nanoparticles and hollow nanocapsules.

The Template

In the present invention, the nanoparticle template can be made from any suitable material, such as a wide variety of inorganic materials including metals or ceramics. Representative metals include chromium, iron, zinc, nickel, gold, silver, tin oxide, iron oxide ($Fe_2O_3$), and platinum. Representative ceramic materials include silicon dioxide, aluminium oxide, ruthenium oxide, and tin oxide. Other materials include calcium or calcium precipitates, such as calcium carbonate. A preferred nanoparticle template is silica. Particles made from the above materials are available commercially.

The template may be of any suitable size or shape. In one aspect, the nanoparticle template is a sphere, a rod, or has an irregular shape. In another aspect, the template has a diameter ranging from about 1 nanometer to about 1,000 nanometers, more preferably from about 5 nanometers to about 500 nanometers, and still more preferably from about 10 nanometers to about 200 nanometers. In still another aspect, the template has an average diameter of about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 175, about 200, about 225, about 250, about 275, about 300, about 325, about 350, about 375, about 400, about 425, about 450, about 475, or about 500 nm, or any range derivable therein.

The Cross-Linker

In one embodiment, the cross-linker of the present invention is preferably an acid-labile cross-linker. That is, the cross-linker is stable under basic conditions, but hydrolyzes rapidly under mildly acidic conditions. For example, the cross-linker is typically stable at a pH greater than about 7 but hydrolyzes significantly at a pH of about 5 or less. More preferably, the cross-linker has an acid-labile ketal, and still more preferably is define according to Formula I:

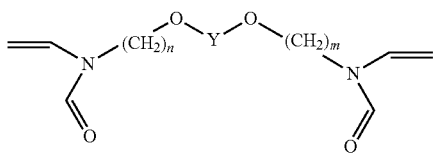

wherein n and m are independently an integer of between 1 and 10; and wherein Y is a lower alkyl.

In a further aspect, the cross-linker is defined according to Formula 2:

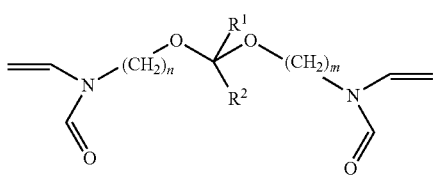

wherein n and m are independently an integer of between 1 and 10; and wherein $R^1$ and $R^2$ are independently a lower alkyl, preferably methyl.

In a preferred aspect, the cross-linker is 2-bis[2,2'-di(N-vinylformamido)ethoxy]propane ("BDEP").

In another embodiment, the cross-linker is not degradable at low pH values. This cross-linker may also be used for the polymerization of NVF to form the PNVF nanoparticles, composite nanoparticles, and nanocapsules of the present invention. In one aspect, the cross-linker is defined according to Formula III:

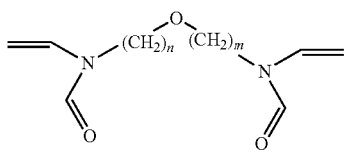

wherein n and m are independently an integer of between 1 and 10.

In a preferred aspect, the acid-stable cross-linker 2-(N-vinylformamido)ethyl ether ("NVFEE").

Polymerizable Monomers

The nanoparticle templates of the present invention are coated with a suitable homopolymers or copolymers to form a polymer shell. Preferred polymerizable monomers are those which form a polymer having an amide side chain, such as N-vinyl formamide and N-vinylacetamide, and copolymerization of N-vinylformide and N-vinylacetamine with different monomers, including but not limited to acrylamides, acrylates, vinyl acetate, etc. Other suitable monomers are found in Lenney et al., U.S. Pat. No. 5,470,903, which is incorporated by reference.

The shell may have a thickness which is thicker than the average particle size (diameter) of the template, a thickness which is thinner than the average particle size of the template, or a thickness which is about equal to the average particle size of the template. In one aspect the shell thickness is less than about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 nm, or any range derivable therein. Preferred shell thickness range between 10 and 100 nm, with shell thickness between 15 and 50 nm being more preferred.

Dissolution of Nanoparticle Template

The composite nanoparticles are converted to hollow polymer capsules via dissolution of the nanoparticle template. Any suitable solvent or etchant can be employed to dissolve the nanoparticle template. For example, nitric acid ($HNO_3$) can be used for dissolving silver (Ag) particles, and ascorbic acid can be used for dissolving iron oxide ($Fe_2O_3$) particles. In addition, either hydrofluoric acid (HF) or sodium hydroxide (NaOH) can be used to etch silica nanoparticles. Typically the solvent or etchant is chosen based on the contemplated end use for the nanocapsule and/or the stability of the cross-linker. The solvent or etchant can be biologically compatible when the nanocapsule is to be used for biological applications.

For example, for gold templates, the composite material may be converted to hollow polymer nanocapsules by soaking a solid support membrane containing composite particles in an aqueous solution of 0.1 M KCN/0.001 M $K_3[Fe(CN)_6]$, or other suitable etchant or solvent for the nanoparticle template. Gold dissolution occurs via transport of etchant species through the polymer shell to the core, where $Au^0$ is converted to $[Au(CN)_4]^-$.

Hydrolysis of PNVF using an aqueous solution of either acidic (e.g., hydrochloric acid) or basic conditions (e.g., sodium hydroxide) results in PVAm according to the following scheme:

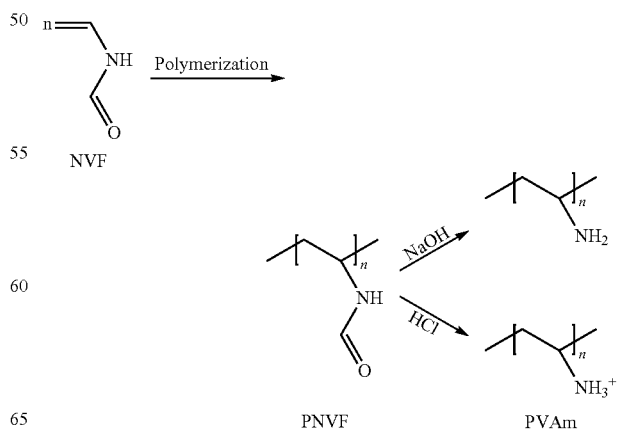

In an exemplary embodiment of present invention, PVAm nanocapsules were obtained by etching the PNVF/silica composite nanoparticles in NaOH under sonication followed by hydrolysis of PNVF through extended exposure to the NaOH aqueous solution (FIG. 1). The pH-sensitive cationic PVAm nanocapsules were able to degrade more quickly at reduced mildly acidic pH values compared to higher near neutral pH values.

PVAm has stable primary amine functionality along its backbone and may be partially or fully hydrolyzed to impart a low or high density polycation, respectively. This polymer has been employed in industrial applications such as ink jet printing, adhesives, industrial coatings, ion exchange resins (for separation-purification purposes), oil field and mining, and textiles. The high reactivity of amino groups provides important active sites for crosslinking and/or derivatization.

In addition, recently, PVAm has been used as a macromolecular carrier for the development of new detection reagents. For example, polyvinylamine-streptavidin conjugates labeled with a europium chelate, were used in combination with biotinylated reagents (e.g., antibodies, DNA probes) for the development of highly sensitive solid-phase, time-resolved, fluorescence-based assays. In addition, PVAm has been demonstrated as an effective gene delivery vector because of its ability to condense DNA, the complex exhibiting high stability and high gene expression in cells.

As discussed more fully below, the size and shell thickness of nanocapsules was easily adjusted by controlling the size of the silica template and the reaction time, respectively. The resulting nanocapsules demonstrated high stability at neutral pH (pH of about 7.4; $t_{1/2}$ greater than 3 days) compared to rapid dissolution observed at lower pH (pH of about 4; $t_{1/2}$ of about 42 minutes). A high degree of swelling occurred in the PVAm nanocapsules as pH decreased, which correlated with the relative charge (zeta potential) of PVAm nanocapsules.

As used herein, a "nanoparticle" is a microscopic particle whose size is measured in nanometers. In preferred embodiments, the nanoparticles of the present invention have a size of from about 1 to about 3000 nanometers. In more particular aspects, the nanoparticle has a size of about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, or more nanometers, or any range derivable therein.

As used herein, the term "nanocapsule" refers to a partially or completely hollow nanoparticle.

As used herein, the term "nanogel" means a water soluble polymer cross-linked to form a nanoparticle, either in solid or capsule form. The nanogels may form a colloidal network when placed in a suitable medium, such as water.

As used herein, the term "lower alkyl" refers to an aliphatic hydrocarbon group which may be straight or branched and comprising about 1 to about 6 carbon atoms in the chain, preferably about 1 to 4 carbons.

In certain embodiments, the nanoparticles, composite nanoparticles, and nanocapsules can be associated with an active ingredient (e.g., entangled, embedded, incorporated, encapsulated, bound to the surface, or otherwise associated with the nanoparticle, composite nanoparticle, or nanocapsule). In certain preferred aspects, the active ingredient is the nanoparticle, composite nanoparticle, or nanocapsule. In a preferred but non-limiting aspect, the active ingredient is a drug such as a pure drug (e.g., drugs processed by crystallization or supercritical fluids, an encapsulated drug (e.g., polymers), a surface associated drug (e.g., drugs that are absorbed or bound to the surface of the nanoparticle, composite nanoparticle, or nanocapsule), or a complexed drugs (e.g., drugs that are associated with the material used to form the nanoparticle, composite nanoparticle, or nanocapsule).

Active ingredients include, but are not limited to, any component, compound, or small molecule that can be used to bring about a desired effect. Non-limiting examples of desired effects of the present invention include diagnostic and therapeutic effects. For example, a desired effect can include the diagnosis, cure, mitigation, treatment, or prevention of a disease or condition. An active ingredient can also affect the structure or function of body part or organ in a subject.

Active ingredients which can be used by the present invention include but are not limited to nucleic acids, proteins and peptides, hormones and steroids, chemotherapeutics, NSAIDs, vaccine components, analgesics, antibiotics, antidepressants, etc. Non-limiting examples of nucleic acids that can be used include DNA, cDNA, RNA, iRNA, siRNA, antisense nucleic acid, peptide-nucleic acids, oligonucleotides, or nucleic acids that are modified to improve stability (e.g., phosphorothioates, aminophosphonates or methylphosphonates).

Proteins and peptides that can be used with the present invention include but are not limited to human growth hormone, bovine growth hormone, vascular endothelial growth factor, fibroblast growth factors, bone morphogenic protein, tumor necrosis factors, erythropoietin, thrombopoietin, tissue plasminogen activator and derivatives, insulin, monoclonal antibodies (e.g., anti-human epidermal growth factor receptor2 (Herceptin), anti-CD20 (Rituximab), anti-CD 18, anti-vascular endothelial growth factor, anti-IgE, anti-CD 11a) and their derivatives, single-chain antibody fragments, human deoxyribonuclease I (domase alfa, Pulmozyme), type-1 interferon, granulocyte colony-stimulating factor, leuteinizing hormone releasing hormone inhibitor peptides, leuprolide acetate, endostatin, angiostatin, porcine factor VIII clotting factor, interferon alfacon-1, and pancrelipase (pancreatic enzymes).

Non-limiting examples of hormones and steroids (e.g., corticosteroids) that can be used include norethindrone acetate, ethinyl estradiol, progesterone, estrogen, testosterone, prednisone and the like.

Chemotherapeutics that can be used include but are not limited to taxol (Paclitaxel), vinblastine, cisplatin, carboplatin, tamoxifen and the like.

Non-limiting examples of NSAIDs include piroxicam, aspirin, salsalate (Amigesic), diflunisal (Dolobid), ibuprofen (Motrin), ketoprofen (Orudis), nabumetone (Relafen), piroxicam (Feldene), naproxen (Aleve, Naprosyn), diclofenac (Voltaren), indomethacin (Indocin), sulindac (Clinoril), tolmetin (Tolectin), etodolac (Lodine), ketorolac (Toradol), oxaprozin (Daypro), and celecoxib (Celebrex).

Vaccine components that can be used include but are not limited to Hepatitis B, polio, measles, mumps, rubella, HIV, hepatitis A (e.g., Havrix), tuberculosis, etc.

Non-limiting examples of analgesics include but are not limited to aspirin, acetaminophen, ibuprofen, naproxen sodium and the like.

Antibiotics include but are not limited to amoxicillin, penicillin, sulfa drugs, erythromycin, streptomycin, tetracycline, clarithromycin, tobramycin, ciprofloxacin, terconazole, azithromycin and the like.

Anti-depressants include but are not limited to Zoloft, fluoxetine (Prozac), paroxetine (Paxil), citalopram, venlafaxine, fluvoxamine maleate, imipramine hydrochloride, lithium, nefazodone and the like.

Other active ingredients that can be used with the present invention include but are not limited to sildenafil (Viagra), acyclovir, gancyclovir, fexofenadine, celecoxib (Celebrex), rofecoxib, androstenedione, chloroquine, diphenhydramine HCl, buspirone, doxazosin mesylate, loratadine, clorniphine, zinc gluconate, zinc acetate, hydrocortisone, warfarin, indinavir sulfate, lidocaine, novocaine, estradiol, norethindrone acetate, medroxyprogesterone, dexfenfluramine, dextroamphetamine, doxycycline, thalidomide, fluticasone, fludarabine phosphate, etanercept, metformin hydrochloride, hyaluronate, tetrazocin hydrochloride, loperamide, ibogaine, clonazepam, ketamine, lamivudine (3TC), isotretinoin, nicotine, mefloquine, levofloxacin, atorvastatin (Lipitor), miconazole nitrate (Monistat), ritonavir, famotidine, simvastatin (Zocor), sibutramine HCl monohydride, ofloxacin, lansoprazole, raloxifene (Evista), zanamivir (Relenza), oseltamivir phosphate, 4-phenylbutyric acid sodium salt, chlorpromazine, nevirapine, zidovudine, and cetirizine hydrochloride (Zyrtec).

Non-limiting examples of additional active ingredients can be found in Physician's Desk Reference 2000, 54th Edition, ISBN: 1563633302, AHFS 99 Drug Information, Amer. Soc. of Health System, ISBN: 1879907917 and U.S. Pat. No. 5,019,400, all of which are incorporated by reference.

Other suitable examples of active ingredients are set forth in Feldheim, U.S. Pat. No. 6,602,932, which is incorporated by reference. In particular, other active ingredients include but are not limited to drugs, polynucleic acid constructs and vectors (such as gene therapy vectors), dyes, imaging agents (including paramagnetic, radioactive and fluorogenic chemical species), chemotherapeutic agents, toxins, radiotherapeutics, radiosensitizing agents or other suitable agent. Typically the imaging agents are chelated using a suitable chelating agent to help avoid toxic effects. Many currently used well-known paramagnetic agents include ferric ammonium citrate, gadolinium-DTPA, chromium-DTPA, chromium-EDTA, manganese-DTPA, manganese-EDTA, manganese chloride, iron sulfate and mixtures thereof. Exemplary contrast agents are disclosed in Brechbiel, U.S. Pat. No. 6,852,842, and Mulder et al., *Lipid-based nanoparticles for contrast-enhanced MRI and molecular imaging*, NMR Biomed. 19(1) 142-64 (2006), which are incorporated by reference. Further, isotopes of the contrast agents are often used for many imaging techniques. Active ingredients may also include metal catalyst particles that can extend the life of the particle by preventing particle agglomeration. Such catalyst particles can be used in nanoparticles, composite nanoparticles, or nanocapsules in chemical catalysis or size-selective environmental waste removal, among other applications.

Pharmaceutical Compositions and Routes of Administration

One embodiment of this invention includes methods of treating, preventing, or diagnosing a particular disease or condition by administering the disclosed nanoparticles, composite nanoparticles, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

Pharmaceutical Compositions

Pharmaceutical compositions of the present invention can include nanoparticles, composite nanoparticles, or nanocapsules of the present invention. The phrases "pharmaceutical or pharmacologically acceptable" can include but are not limited to molecular entities and compositions that do not produce an adverse, allergic or other untoward reaction when administered to a subject, such as, for example, a human. The preparation of a pharmaceutical composition is generally known to those of skill in the art. Remington's Pharmaceutical Sciences, 18th Ed. Mack Printing Company, (1990). Moreover, for animal (e.g., human) administration, it is preferred that the preparations meet sterility, pyrogenicity, general safety, and purity standards as required by the FDA Office of Biological Standards.

"Therapeutically effective amounts" are those amounts effective to produce beneficial results in the recipient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

"Pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

The actual dosage amount of a composition of the present invention administered to a subject can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The composition may also include various antioxidants to retard oxidation of one or more active ingredient or nanoparticles, composite nanoparticles, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may include different types of carriers depending on whether it is to be administered in solid, liquid or aerosol form, and whether it need to be sterile for such routes of administration as injection.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid, or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

In another aspect of the present invention, a person of ordinary skill will recognize that the compositions of the present invention can include any number of combinations of nanoparticles, composite nanoparticles, nanocapsule, active ingredients, and other components. It is also contemplated that that the concentrations of these ingredients can vary. For example, in one-non-limiting aspect, a composition of the present invention can include at least about 0.0001% to about 0.001%, about 0.001% to about 0.01%, about 0.01% to about 0.1%, or about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the nanoparticles, nanogels, composite nanoparticles, nanocapsules, active ingredients, or other components that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of nanoparticles, composite nanoparticles, or nanocapsules, active ingredients, and other components.

Routes of Administration

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, intrathecally, topically, intratumorally, intramuscularly, intraperitoneally, subcutaneously, subconjunctival, intravascularly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

Combination Therapies

In order to increase the effectiveness of a treatment with the nanoparticles, nanogels, composite nanoparticles, or nanocapsules of the present invention, it may be desirable to combine these nanoparticles, composite nanoparticles, or nanocapsules with other therapies effective in the treatment of a particular disease or condition.

The compositions of the present invention, for example, can precede or follow the other agent treatment by intervals ranging from minutes to weeks. It is contemplated that one may administer both modalities within about 12-24 hours of each other and, more preferably, within about 6-12 hours of each other. In some situations, it may be desirable to extend the time period for treatment significantly, where several days (2, 3, 4, 5, 6, or 7), several weeks (1, 2, 3, 4, 5, 6, 7, or 8) or even several months (1, 2, 3, 4, 5, 6, or more) lapse between the respective administrations.

Various combinations may be employed where a compositions including a nanoparticles, composite nanoparticles, or nanocapsules is "A" and the secondary agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A.

The following examples are included to demonstrate certain non-limiting aspects of the present invention.

In the examples, N-vinyl formamide (NVF; Aldrich) was distilled under vacuum and stored at about −18° C. prior to use. The initiator, 1,1'-azobisisobutyronitrile (AIBN; Aldrich), was recrystallized from ethanol. All other materials were used without further purification including: 1-octanol (Fischer Scientific), tetraethoxysilane (TEOS; Aldrich) and 3-methacryloxypropyltrimethoxysilane (MPS; Aldrich), potassium t-butoxide (Aldrich) and 2-bromoethyl ether (tech, 90%; Aldrich), anhydrous tetrahydrofuran (THF; Aldrich), and poly(vinylpyrrolidone) (PVP, Mw=360,000; Sigma). The pure water used was obtained from a Barnstead NANOpure water purifier. Silica particles were prepared as described previously in Stöber et al., *Controlled Growth of Monodisperse Silica Spheres in the Micron Size Range*, J. Colloid Interface Sci. 1968, 26, 62-69 (1968). MPS-coated silica particles as seeds were prepared as described previously in Bourgeat-Lami et al., *Encapsulation of inorganic particles by dispersion polymerization in polar media*-1. *Silica nanoparticles encapsulated by polystyrene*, Journal of Colloid and Interface Science 197, (2), 293-308 (1998). In addition, 2,2-dibromoethoxypropane was prepared according to Lorette et al., *Preparation of Ketals from 2,2-Dimethoxypropane*, J. Org. Chem. 25, 521-525 (1960).

Example 1A

Synthesis of 2-bis[2,2'-di(N-vinylformamido)ethoxy]propane ("BDEP")

Figure 2:
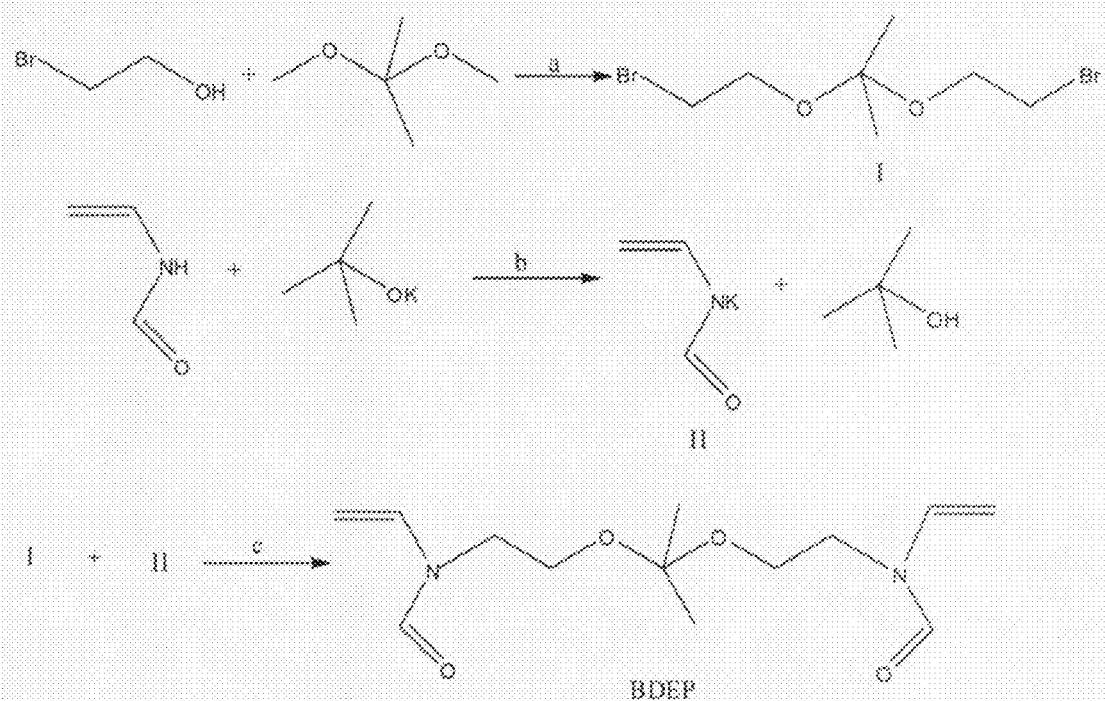
FIG. 2 is a schematic representation of the synthesis of the cross-linker 2-bis[2,2'-di(N-vinylformamido)ethoxy]propane ("BDEP").

A few cross-linkers containing acid-labile ketals have been reported. See Murthy, et al., *A novel strategy for encapsulation and release of proteins: Hydrogels and microgels with acid-labile acetal cross-linkers*, Journal of the American Chemical Society 124 (42) 12398-12399 (2002); Srinivasachar et al., *New Protein Cross-Linking Reagents That Are Cleaved by Mild Acid*, Biochemistry 28 (6) 2501-2509 (1989); Ruckenstein et al., *A novel breakable cross-linker and pH-responsive star-shaped and gel polymers*, Macromolecules 32 (12) 3979-3983 (1999). However, these cross-linkers are not generally suitable for the present invention because they all contain either ester or amido bonds, which are unstable under strongly basic conditions (hydrolysis of ester or amido bonds destroys crosslinking points). Therefore, in the present invention, a novel acid-labile cross-linker, BDEP, which is stable under basic conditions was prepared (FIG. 2).

The new acid-labile cross-linker was synthesized by the reaction of N-vinyl formamide potassium salt with 2,2-dibromoethoxypropane (I), which was synthesized according to the method described in literature. See Fleming et al., *Nanosphere-microsphere assembly. Methods for core-shell materials preparation*, Chemistry of Materials 13 (6) 2210-2216 (2001). The synthetic procedure included two steps. In the first step, N-vinyl formamide potassium salt was prepared by the reaction of N-vinyl formamide with potassium t-butoxide in anhydrous tetrahydrofuran in an ice bath. In the second step, the desired cross-linker, BDEP, was obtained by the addition of the compound (I) into the suspension of N-vinyl formamide potassium salt in anhydrous THF in the presence of the phase-transfer catalyst dicyclohexyl-18-crown affording an overall yield of 86%. Here the phase-transfer catalyst dicyclohexyl-18-crown played a critical role in the improvement of the yield of product. The yield is only about 10% in the absence of the phase transfer catalyst. BDEP is collected as a white needle-like crystal and is soluble in most polar solvents such as ethanol and acetone.

More specifically, a mixture of N-vinyl formamide (10.23 g, 0.144 mol), potassium t-butoxide (16.47 g, 0.144 mol) and dicyclohexyl-18-crown (2 g, 5.3 mmol) in anhydrous THF (200 mL) was stirred vigorously at room temperature for 45 minutes and then cooled in an ice bath. 2,2-dibromoethoxypropane (17.02 g, 58.6 mmol) was added dropwise for 1 hour and then the mixture was stirred at room temperature for 48 hours. After potassium bromide salt was removed, the reaction mixture was concentrated under reduced pressure and diluted with 200 mL of water. The crude product was obtained by extraction with CHCl$_3$ 5 times (50 mL×5). The combined organic layers were washed twice with brine and dried over anhydrous sodium sulfate. The resulting product was recovered after concentration in vacuo and purification by chromatograph on silica (ethyl acetate/hexane (v/v=8:2); yield: 86%. BDEP structure was then confirmed by IR, NMR, and mass spectroscopy.

IR (NaCl, v: cm$^{-1}$): 1680 (—NHC(=O)H); 1630 (C=C).
$^1$H-NMR (CDCl$_3$, δ, ppm): 8.33, 8.32, 8.13 (m, 2H, —C(=O)H); 7.22-7.19, 6.63-6.57 (m, 2H, H$_2$C=CH—); 4.74-4.43 (m, 4H, CH$_2$=CH—); 3.73-3.44 (m, 8H, —CH$_2$CH$_2$—); 1.30-1.28 (t, 6H, —CH$_3$).
$^{13}$C-NMR (CDCl$_3$, δ, ppm): 24.48, 40.63, 40.75, 45.28, 56.72, 57.14, 57.47, 94.40, 94.76, 94.90, 100.17, 100.40, 128.63, 128.74, 133.51, 133.70, 161.98, 162.63, 162.81. Mass calculated for C$_{13}$H$_{22}$N$_2$O$_4$: 270.1579, FOUND (EI): 270.1591.

It will be appreciated to those skilled in the art that compounds of Formula I and II may be prepared, for example, by modification of the starting materials. Exemplary starting materials include but are not limited to 2,2-dibromopropoxypropane, 2,2-dibromobutoxypropane, 2,2-dibromobutoxypropane, 2,3-dibromoethoxypropane, 2,3-dibromopropoxypropane, 2,3-dibromopropoxybutane, and other similar dibromoalkoxyalkyl materials.

Example 1B

Synthesis of 2-(N-vinylformamido)ethyl ether

In this example, a novel non-degradable cross-linker was prepared. More specifically, a mixture of N-vinylformamide, potassium t-butoxide and dicyclohexyl-18-crown in anhydrous THF was stirred vigorously at room temperature for 45 minutes and then cooled in ice bath. Next, 2-bromoethyl ether was added dropwise for 1 hour and then the mixture was stirred at room temperature for 48 hours. After potassium bromide salt was removed, the reaction mixture was concentrated under reduced pressure and diluted with 200 ml of water. The crude product was obtained by extraction with CHCl$_3$ 5 times. (50 ml×5). The combined organic layers were washed twice with brine and dried over anhydrous sodium sulfate. The resulting product was recovered after concentration in vacuo and purification by chromatograph on silica (ethyl acetate/hexane (v/v=8:2). The purified product is yellowish oil and yield was 86%.

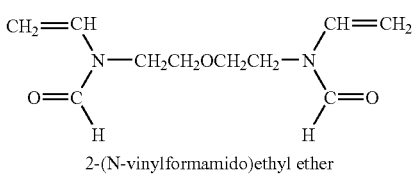

2-(N-vinylformamido)ethyl ether

IR (NaCl, v: cm$^{-1}$): 1688 (—NHC(=O)H); 1632 (C=C).
$^1$H-NMR (CDCl$_3$, δ, ppm): 8.38, 8.08, 8.05 (m, 2H, —C(=O)H); 7.11-7.03, 6.80-6.72 (m, 2H, H$_2$C=CH—); 4.93-4.63 (m, 4H, CH$_2$=CH—); 3.85-3.72 (m, 8H, —CH$_2$CH$_2$—).

$^{13}$C-NMR (CDCl$_3$, δ, ppm): 39.99, 45.14, 66.50, 66.86, 67.35, 94.43, 94.64, 128.59, 133.32, 161.56, 161.84, 162.59, 162.68.
MS calcd for C$_{10}$H$_{16}$N$_2$O$_3$: 212.1160, FOUND (EI): 212.1169.

Alternatively, a mixture of N-vinylformamide, potassium carbonate (8 g), sodium hydroxide (14 g) and tetra-n-butylaminium hydrogen sulfate (3.4 g) and benzene (100 ml) was stirred vigorously at temperature of 47° C. for 1 hour. The solution of 2-bromoethyl ether (8.6 g) in benzene (50 ml) was added dropwise with stirring to the above mixture at 65° C. and maintained that temperature for 5 hours. The resultant mixture was cooled down to room temperature. Filtered and the precipitate was washed with benzene (50 ml×2) and the washings are combined with the filtrate. The benzene solution was washed with Na$_2$CO$_3$ (5 wt %) (50 ml×3). The organic phase was dried over anhydrous sodium sulfate and evaporated to give crude product as dark brown oil. The resulting product was recovered after concentration in vacuo and purification by chromatograph on silica (ethyl acetate/hexane (v/v=8:2). The purified product is yellowish oil and yield was 57%.

It will be appreciated to those skilled in the art that compounds of Formula III may be prepared, for example, by modification of the starting materials. Exemplary starting materials include but are not limited to Bis(2-bromopropyl) ether, Bis(2-bromobutyl)ether, and other similar dibromo ethers.

Example 2

Preparation of PNVF Shell/Silica Particle Core Composite Nanoparticles

In this example, composite nanoparticles comprising a silica core and a PNVF shell were prepared. Coating of silica nanoparticles with the PNVF shell was carried out by dispersion graft copolymerization of N-vinyl formamide (NVF) and the cross-linker (BDEP) in the presence of PVP (MW=360 kDa) in ethanol at 70° C. In order to successfully achieve coating of PNVF around the silica particles, vinyl groups were introduced onto the silica nanoparticle surface prior to polymerization by using the coupling agent methacryloxypropyltrimethoxysilane ("MPS"), which contains a vinyl group at one terminus. Vinyl groups on the particle surface allowed covalent attachment and growth of PNVF from the particle surface by copolymerization with NVF and BDEP. See Tissot et al., *Hybrid latex particles coated with silica.* Macromolecules 34 (17) 5737-5739 (2001); Chaimberg et al., *Graft-Polymerization of Polyvinylpyrrolidone onto Silica*, Journal of Applied Polymer Science 37 (10), 2921-2931 (1989).

An exemplary procedure is as follows. To a suspension of MPS-modified silica particles (0.5 g) in ethanol (40 mL) was charged NVF (1.25 g), cross-linker (BDEP; 0.66 g), PVP (0.75 g) and AIBN (0.033 g) under stirring. After removing oxygen by bubbling with nitrogen for 15 minutes, the suspension was heated to 70° C. and maintained at that temperature for 60 minutes. The composite particles were purified by centrifugation/dispersion for five cycles using ethanol.

Figure 3:
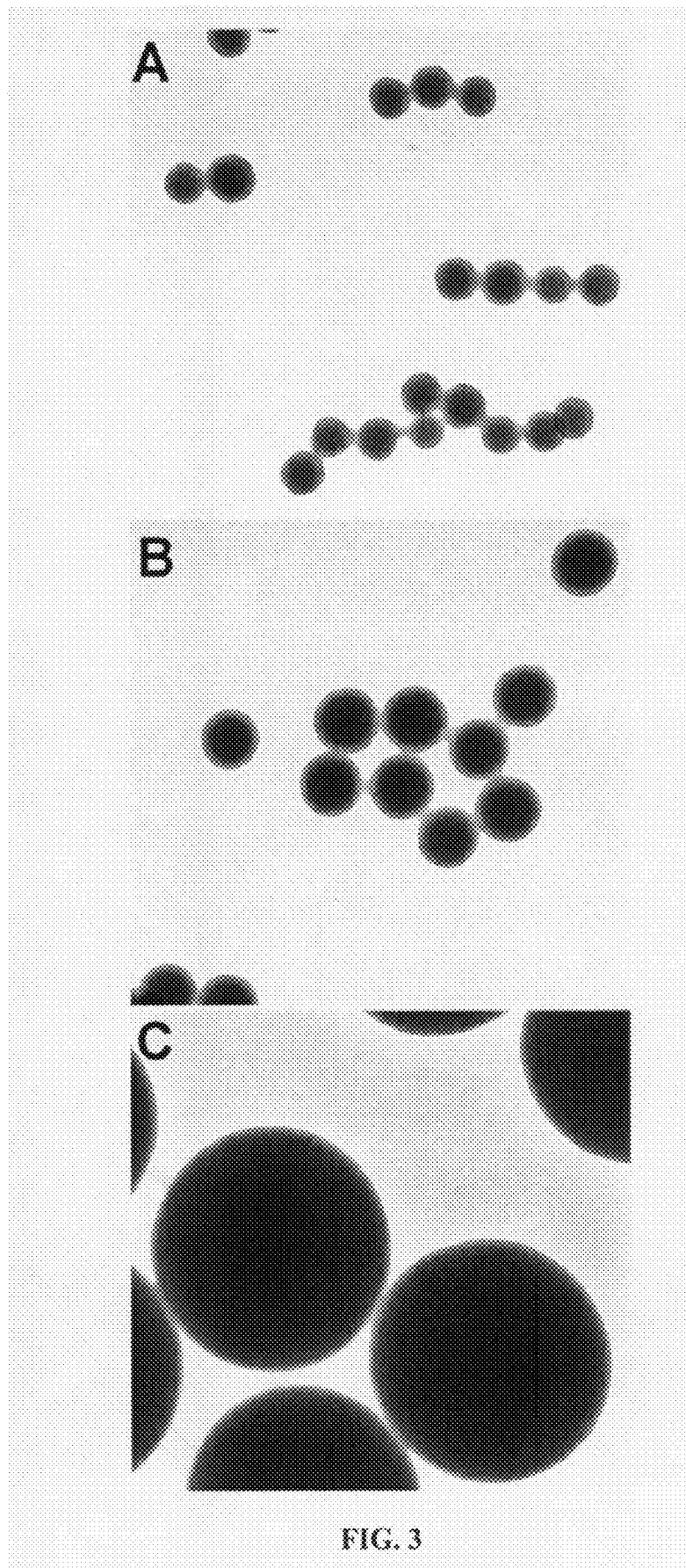
FIG. 3 shows the fabrication of PNVF shell/silica core composite nanoparticles using different size silica templates prepared in ethanol in the presence of polyvinyl pyrrolidone ("PVP") as a stabilizer at 70° C. Panel A shows silica particles (83±5.3 nm) with a PNVF shell (23±2.0 nm). Panel B shows silica particles (192±10.2 nm) with a PNVF shell (19±1.0 nm). Panel C shows silica particles (800±5.1 nm) with a PNVF shell (17±1.0 nm).
Figure 4:
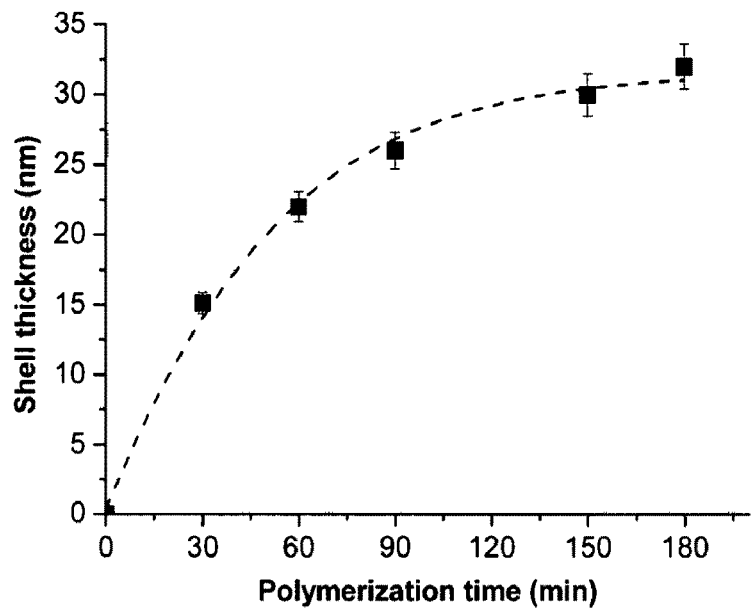
FIG. 4 shows the PNVF shell thickness as a function of polymerization time using the methods described herein. The average particle size of the silica particles was about 165 nm, and the polymerization occurred at about 70° C.

A series of PNVF shell/silica core composite nanoparticles were synthesized under the same polymerization conditions using silica particles ranging from about 83 nm to 800 nm in diameter (FIG. 3). A very thin PNVF shell (17±1.0 nm) was detectable on the surface of the largest silica nanoparticles while relatively thicker shells (23±2.0 nm) are evident on the smallest silica nanoparticles. The shell thickness of PNVF composite nanoparticles was readily controlled by controlling the polymerization time (FIG. 4). PNVF shell thickness increased with polymerization time due to the increase in monomer conversion with time and curtailed as monomer was consumed. The PNVF shell/silica core nanocomposites were easily dispersed in water, ethanol and t-butanol. Maintaining the polymerization temperature lower than 70° C. was necessary to produce pure nanocomposites as temperatures above 70° C. may result in the production of a large amount of PNVF nanoparticles. The formation of PNVF nanoparticles is probably ascribed to the high reactivity of NVF and transfer of PNVF chain free-radicals to PVP in the solution (NVF: $C_m = 9.37 \times 10^4$ at 60° C.), see Gu et al., *Kinetics and modeling of free radical polymerization of N-vinyl formamide*, Polymer 42 (7) 3077-3086 (2001), which produces new particle nuclei leading to the formation of PNVF particles. See Uyama et al., *Preparation of Monodisperse Poly(N-Vinyl formamide) Particles by Dispersion Polymerization in Methanol Solvent*, Chemistry Letters (2) 261-262 (1993).

Example 3

Preparation of PNVF and Polyvinylamine (PVAm) Nanocapsules

In this example, hollow nanocapsules were prepared using the nanoparticles prepared in Example 2. In general, the nanoparticle template was removed using a suitable etchant. In this case, sodium hydroxide (NaOH), was used to easily dissolve silica particles with the aid of sonication at room temperature to form the PNVF nanocapsules. The concentration of NaOH required is directly dependent on the amount of silica particles to be etched. The acid-labile PVAm nanocapsules were then successfully prepared PNVF hydrolysis in NaOH at 80° C. One of the advantages of using this method is that the conversion of amino groups of nanocapsules can be controlled by simply controlling hydrolysis time.

More specifically, PNVF nanocapsules were fabricated by etching silica in 1M NaOH aqueous solution under sonication at room temperature. Typically, PNVF shell/silica core composite nanoparticles (0.4 g) were dispersed into 1M NaOH (40 mL) and sonicated at room temperature in a sonicating tank for about 60 minutes. The nanocapsules obtained were purified by dialysis against water at pH 9.0 for 24 hours. This procedure resulted in the production of PNVF nanocapsules that were about 30% hydrolyzed.

PVAm nanocapsules were then produced by subsequently hydrolyzing the shell polymer. More specifically, hydrolysis of the PNVF shell in 1M NaOH at 80° C. for 12 hours produced PVAm nanocapsules (about 100% hydrolyzed).

FTIR Spectra

FTIR spectra were recorded on a MB-104 FT-IR Spectrometer (ABB Bomen Inc.). A Bruker AMX 500 spectrometer was used to record the NMR spectra of compounds synthesized using $CDCl_3$ as a solvent and tetramethylsilane as an internal standard. Particle sizes and size distributions were determined by quasi-elastic light scattering (QELS). QELS measurements were performed at a 90° scattering angle with a Brookhaven BI-MAS. The cumulant method was used to determine the effective diameter and polydispersity index ($\sigma$). In the cumulant analysis, the logarithm of the autocorrelation function is expressed as a polynomial in the delay time (t). The polydispersity index ($\sigma$) is defined as $\sigma = \mu_2/\Gamma^2$, where $\Gamma$ and $\mu_2$ are the first two cumulants of the distribution. $\sigma$ is close to zero for nearly monodisperse samples, small (0.020 to 0.080) for narrow size distributions, and large for broad distributions.

Figure 5:
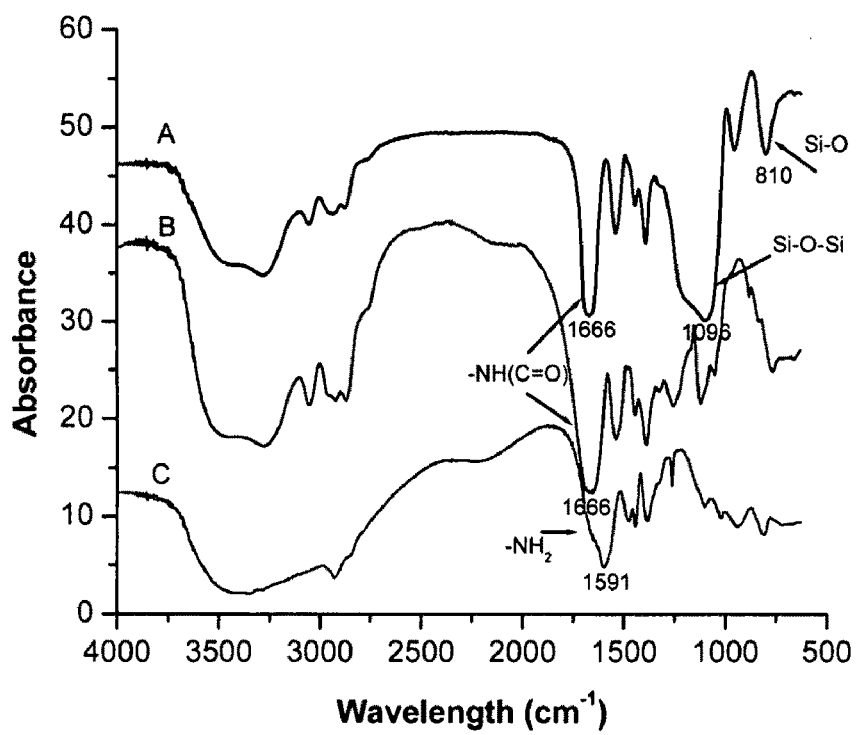
FIG. 5 shows the IR spectra verified chemical signatures of PNVF-shell/silica core composite nanoparticles (line A), PNVF nanocapsules after silica etching (about 30% conversion of formamido to amino) (line B), and PVAm nanocapsules (about 100% conversion) (line C).

FTIR spectra verified each step of the fabrication process: (1) PNVF shell/silica core nanocomposites crosslinked by BDEP, (2) PNVF nanocapsules after silica was etched in 1M NaOH at room temperature for 60 minutes, and (3) the resulting PVAm nanocapsules after hydrolysis in 1M NaOH aqueous solution at 80° C. for 24 hours, respectively (FIG. 5). Compared to the peaks in the PNVF shell/silica core nanocomposites (FIG. 5, line A), the peaks at 1096 cm$^{-1}$ (Si—O—Si asymmetric stretching) and 811 cm$^{-1}$ (Si—O bending) disappeared in the PNVF nanocapsules (FIG. 5, line B), which suggests that the silica particle templates were effectively removed by etching in 1M NaOH at room temperature for 60 minutes. The peak at 1666 cm$^{-1}$ in spectrum A and B is a characteristic peak of formamide groups in PNVF, which indicates that PNVF composite nanoparticles and nanocapsules were produced, respectively. It was suspected that the etching process may hydrolyze some of the formamido side groups along the polyvinyl backbone. Although the FTIR spectrum did not distinctly show characteristic peaks of amino side groups on the PNVF nanocapsules, $^1$H-NMR revealed that about 30% of formamido groups were converted into amino groups. The disappearance of the peak at 1666 cm$^{-1}$ and appearance of a new peak at 1591 cm$^{-1}$ after extended treatment of PNVF nanocapsules with 1M NaOH proved that PVAm nanocapsules were produced under the given hydrolysis conditions (formamido conversion about 100%).

TEM Images

Figure 6:
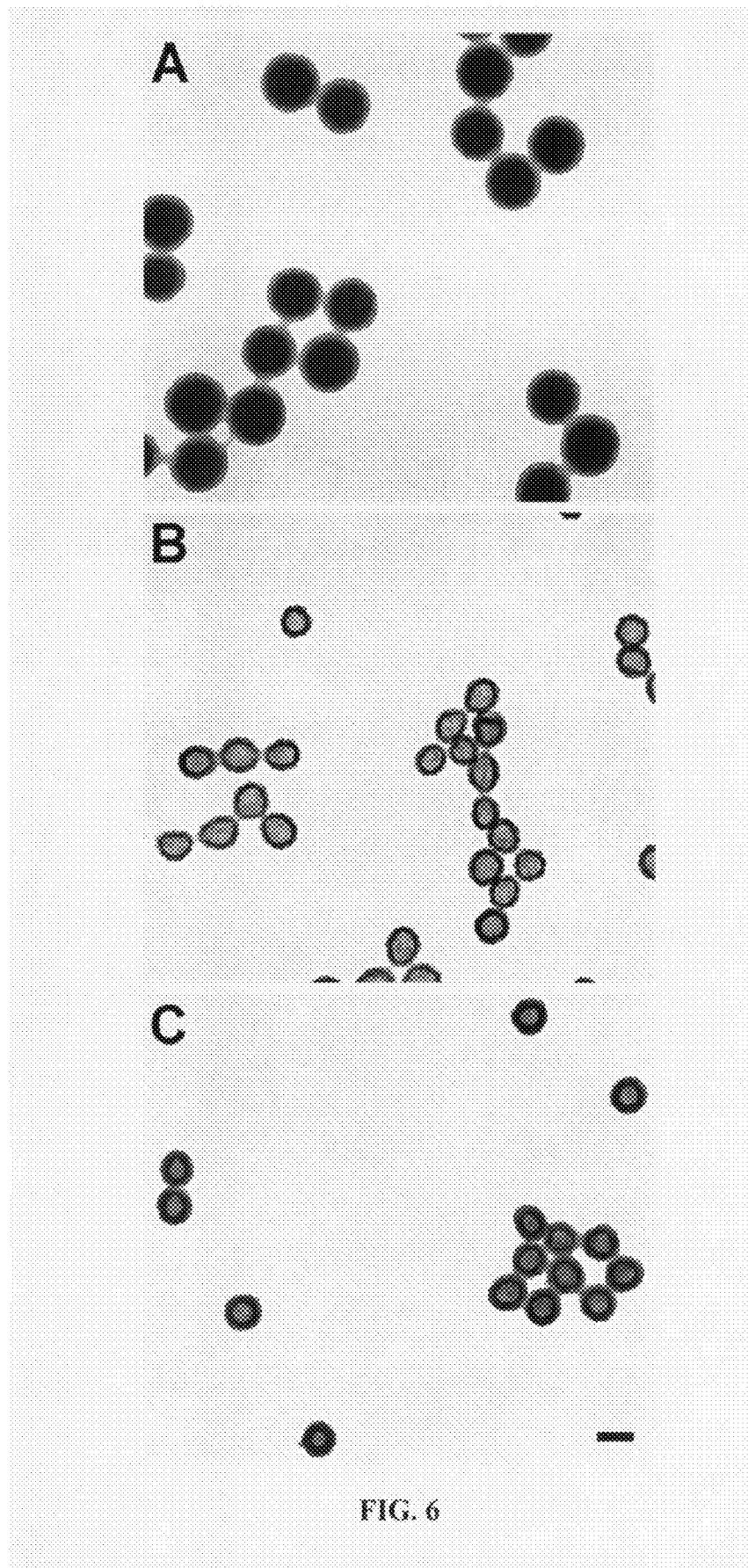
FIGS. 6A-C are TEM images of the PVAm nanocapsule fabrication process confirmed each step. Panel A shows PNVF shell/silica core composite nanoparticles having a PNVF shell thickness of 18±1.0 nm and a core diameter of 127±6.2 nm. Panel B shows PNVF nanocapsules having a PNVF shell thickness of 19±1.0 nm and a core diameter of 68±7.3 nm. Panel C shows PVAm nanocapsules with a PVAm shell thickness of 23±0.5 nm and a meter of 57±3.9 nm.

TEM images of nanoparticles and nanocapsules were obtained using A JEOL 1200 EXII transmission electron microscope operating at an accelerating voltage of 80 kV. The TEM images provided supporting evidence of the nanocapsule fabrication process (FIG. 6). Crosslinked PNVF shell/silica core nanocomposites (FIG. 6A), PNVF nanocapsules after silica was etched out in 1 M NaOH at room temperature for 60 minutes (FIG. 6B), and PVAm nanocapsules after hydrolysis in 1 M NaOH aqueous solution at 80° C. for 12 hours (FIG. 6C) were clearly depicted by TEM. The inner diameter of both PNVF and PVAm nanocapsules became smaller than that of the corresponding silica nanoparticles used as templates due to the shrinkage of nanocapsules upon evaporation of ethanol during TEM sample preparation. In solution at pH higher than about 11.0, the PNVF nanocapsules exhibited a diameter close to the corresponding PNVF nanocomposites prior to silica etching. Uniform shell sizes and inner diameters of both PNVF and PVAm nanocapsules are evident. The PVAm nanocapsule shell (23±0.5 nm) was significantly thicker than the corresponding PNVF nanocapsule shell (19±1.0 nm), even in the dried state. The core diameter was also decreased in PVAm nanocapsules (57±3.9 nm) as compared to PNVF nanocapsules (68±7.3 nm). It is hypothesized that the highly charged PVAm produces swelling due to charge repulsion within the crosslinked polymer. This phenomena is expanded upon below.

Example 4

Dissolution/Degradation Kinetics of PVAm Nanocapsules

In this example, the dissolution/degradation kinetics of nanocapsules at various pH values was determined by using an 8453 UV/Visible Spectrophotometer (Agilent Technologies). About 10 mg of PVAm nanocapsules was placed into a cuvette containing 3 mL of buffer solution at a given pH. The absorbance was measured at a fixed wavelength of 480 nm at 25° C. at preselected time intervals. The pH of the suspension of PVAm nanocapsules was monitored by XL15 pH meter (Accument, Fisher Scientific) with a pH electrode (Thermo Electron Corporation). Concentrations of nanocapsules in suspension were chosen so that the initial optical density of the particle suspension was close to 100%.

Figure 7A:
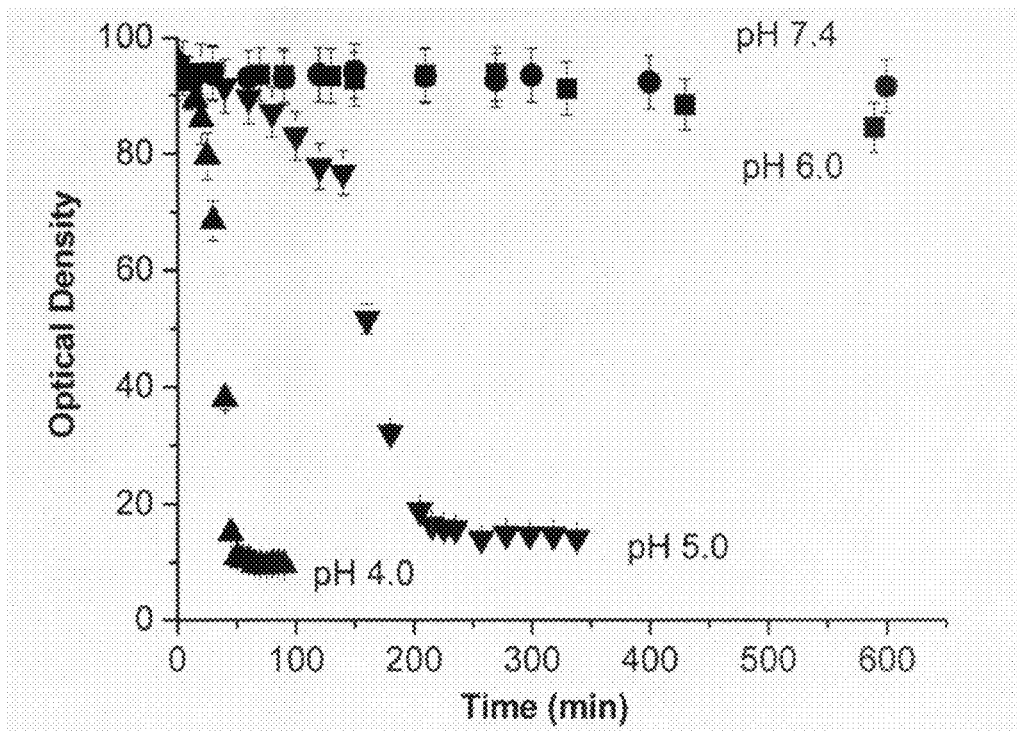
FIG. 7A shows turbidity measurements of PVAm nanocapsules over time as a function of four different pH values (pH of 7.4, 6.0, 5.0, and 4.0).

The results of the turbidity assay are shown in FIG. 7A. Degradation of PVAm nanocapsules occurred rapidly at mildly acidic pH values. Conversely, the slight decrease in optical density of the suspension at higher pH values (6.0 and 7.4) indicated that the nanoparticles degraded much more slowly. The relative half life of PVAm nanocapsules was estimated from the midpoint of the optical density curve (Table 1).

TABLE 1

The half-life of degradation of PVAm nanocapsules as a function of pH

| | pH | | | |
|---|---|---|---|---|
| | 4.0 | 5.0 | 6.0 | 7.4 |
| Half-life ($t_{1/2}$) | 42 minutes | 160 minutes | about 24 hours | More than 3 days |

The degradation of PVAm nanocapsules in acidic buffer was ascribed to the breakdown of ketal-containing crosslinks in the PVAm shell. The degradation kinetics of PVAm nanocapsules was strongly dependent on the pH of the surrounding milieu because the hydrolysis rate of ketals under acid catalyst is proportional to the hydronium ion concentration in solution. See Cordes et al., *Mechanism and catalysis for hydrolysis of acetals, ketals, and ortho esters*, Chemical Reviews 74 581-603 (1974). For example, it has been demonstrated that ketals were hydrolyzed approximately 250 times faster at pH 5.0 than at pH of 7.4 for the case of solid microgels. See Kwon et al., *Directed antigen presentation using polymeric microparticulate carriers degradable at lysosomal pH for controlled immune responses*, Molecular pharmaceutics 2 (1), 83-91 (2005).

Figure 7B:
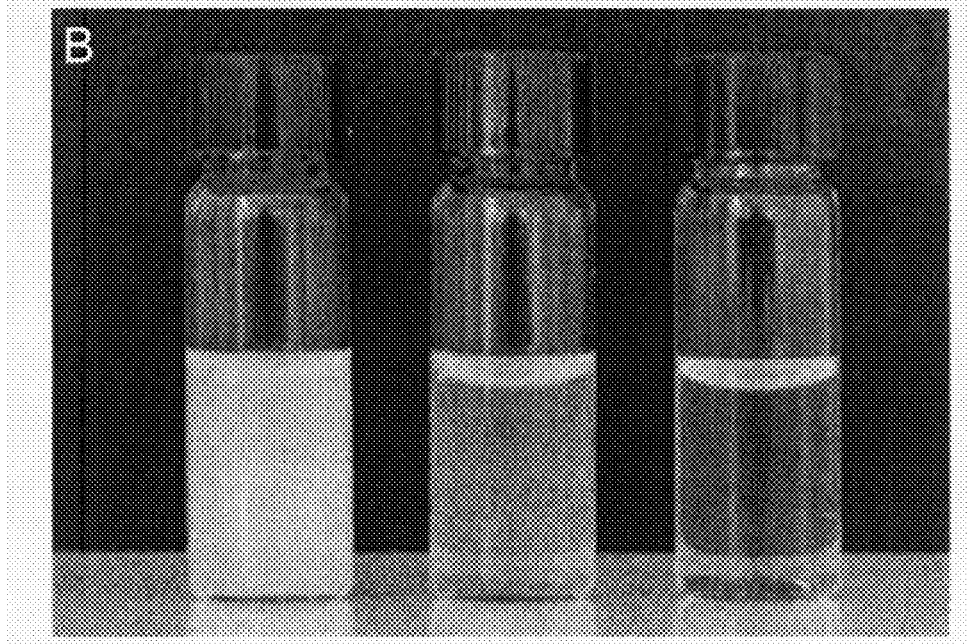
FIG. 7B shows confirmation by visualisation of the degradation of PVAm nanocapsules into soluble PVAm in buffer having a pH of about 5.0 over time.

The degradation of PVAm nanocapsules was also confirmed by visually tracking solution opacity at a pH of about 5.0 over 5 hours (FIG. 7B). The initially opaque PVAm nanocapsule suspension at pH 5 turned completely clear within 300 minutes, which indicated that all particles were degraded and that PVAm oligomers were dissolved in the medium.

Figure 8A:
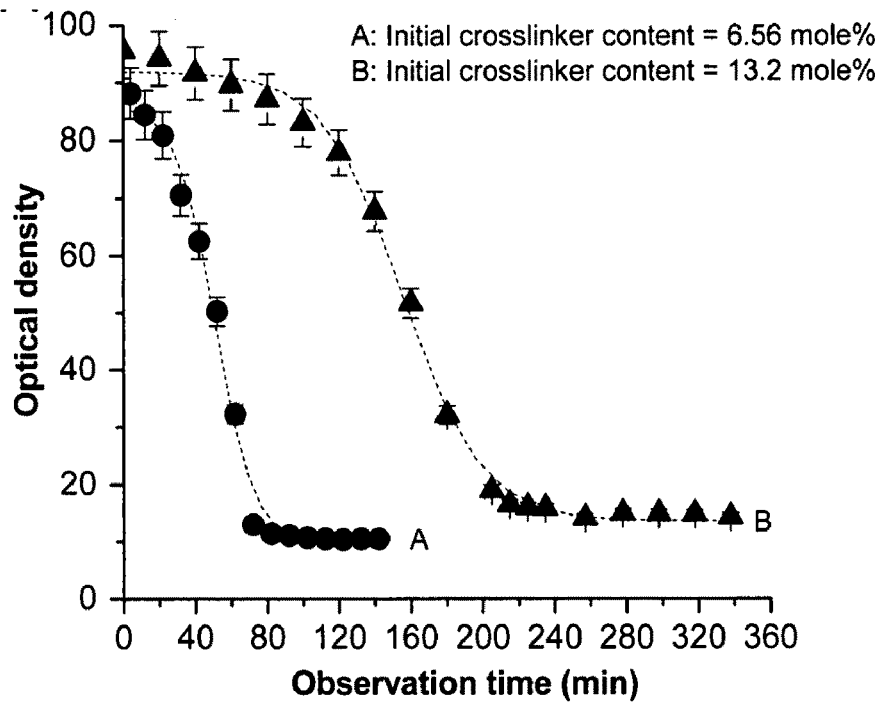
In FIG. 8A, the degradation rate of PVAm nanocapsules is shown at two different crosslinking densities.
Figure 8B:
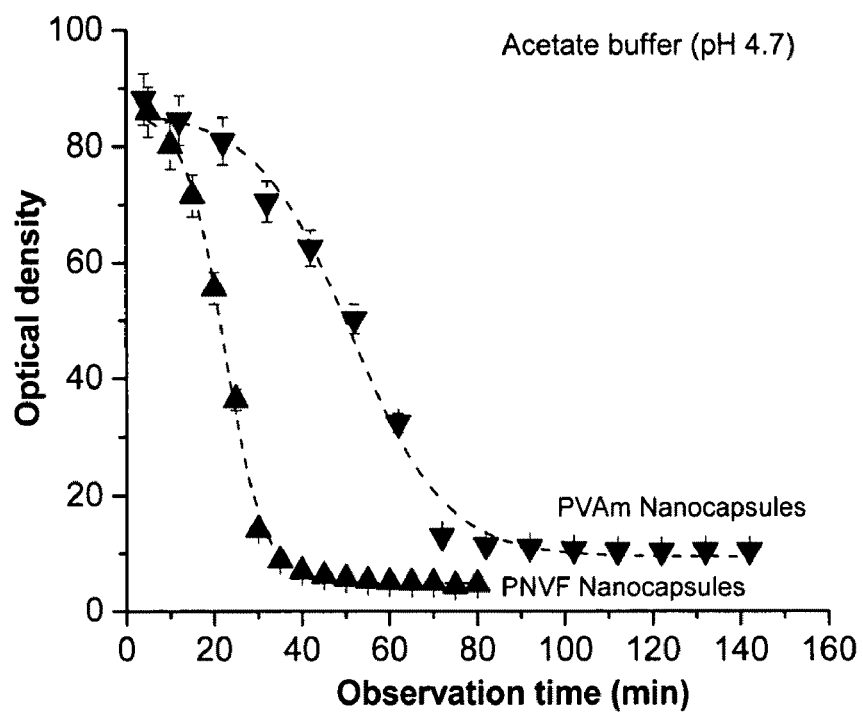
In FIG. 8B, the degradation rate as a function of capsule hydrolysis is shown. PVAm nanocapsules were about 100% hydrolyzed while the PNVF nanocapsules were only about 30% hydrolyzed. Degradation was faster for PNVF nanocapsules (▲) compared to the PVAm nanocapsules (▼) under mildly acidic conditions (pH of about 4.7).
Figure 8C:
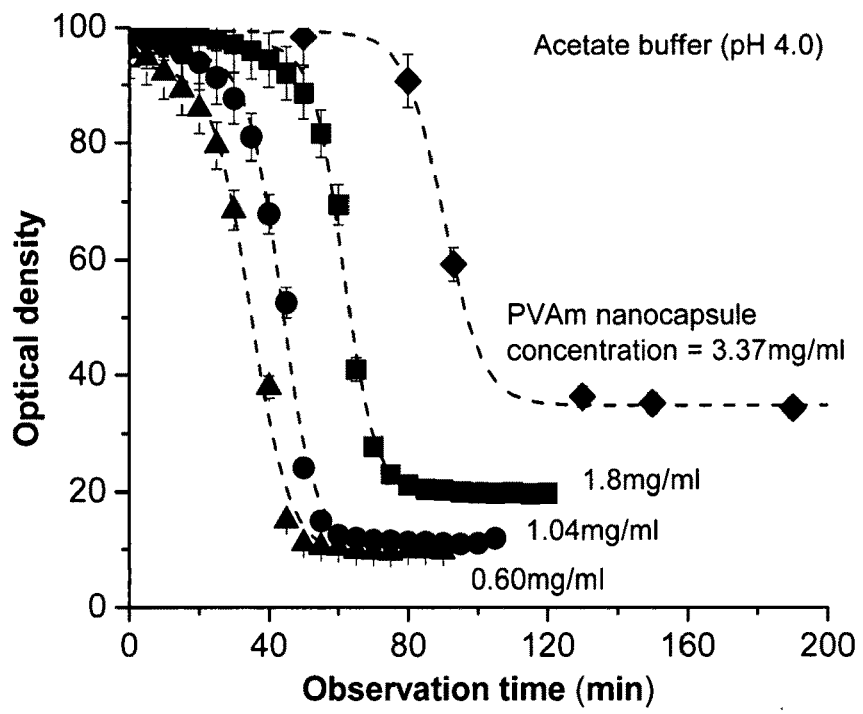
FIG. 8C shows the degradation rate as a function of PVAm nanocapsule concentration at four different concentrations (3.4, 1.8, 1.04, and 0.6 g/ml).
Figure 8D:
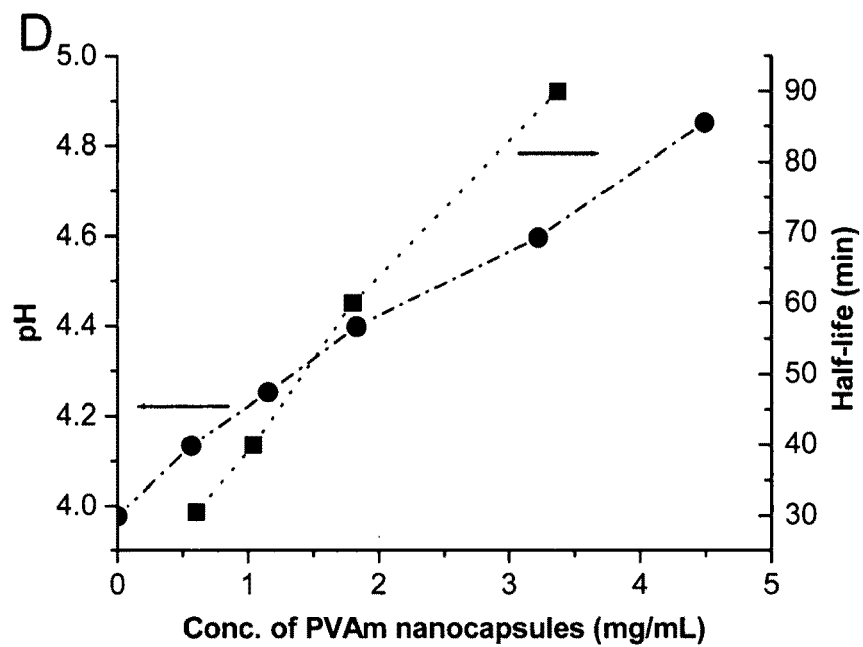
FIG. 8D shows that an increase in the pH of medium (circles ●) as a function of increasing PVAm capsule concentration led to a decrease in the degradation rate (i.e., half-life) (squares ■) of PVAm nanocapsules.

Multiple factors directly influenced the degradation kinetics of the two types of polyvinyl nanocapsules. In the present invention, the extent of crosslinking may be manipulated to adjust the degradation rate of nanocapsules. For example, doubling the molar content of cross-linker from 6.56% to 13.2% in PVAm nanocapsules resulted in an about 3-fold increase in nanocapsule half life at pH 5.0 and produced more gradual degradation kinetics (FIG. 8A). Interestingly, the presence of amino side groups also dramatically affected the degradation of nanocapsules. $^1$H-NMR was used to confirm that about 30% of the formamido side groups were converted to amido side groups during the etching of silica nanoparticle templates to form PNVF nanocapsules (data not shown). At pH 4.7, PNVF nanocapsules (about 30% amino conversion) exhibited about 2.5 fold shorter half life than PVAm nanocapsules that contained about 100% amino conversion (FIG. 8B). The presence of the amino side groups may have a localized buffering effect in that hydronium ions necessary to break the ketal cross-linker associated with amino groups in the capsule matrix. Therefore, increasing the percentage of hydrolyzed formamido side groups may have provided more sites for hydronium ion capture and extend the degradation half life of nanocapsules. This hypothesis was further supported by observing the effect of PVAm nanocapsule concentration on the degradation half life (FIG. 8C). Increasing the concentration of PVAm nanocapsules (about 100% hydrolyzed) increased the pH of the dissolution media and linearly increased the degradation half life (FIG. 8D). For the PVAm nanocapsule concentrations studied, the original solution was buffered at pH 4; however, the reduction in cross-linker degradation as nanocapsule concentration increased may again be attributed to the ability of amino side groups to occupy hydronium ions (buffering effect). Finally, the localized buffering effect may be reflected in the sigmoidal degradation kinetics for all formulations, which do not follow linear ketal degradation.

Example 5

Comparison of Charge and Swelling of PNVF and PVAm Nanocapsules

In this example, nanocapsules were conjugated with FITC. More specifically, PVAm nanocapsules (100 mg) were dispersed in sodium bicarbonate buffer at pH 9 (5 mL). Fluoroisothiocyanate (FITC; 11.07 mg) was dissolved in dry DMSO (5 mL), added to the PVAm nanocapsule dispersion, and stirred overnight at room temperature. FITC-conjugated PVAm nanocapsules were purified by centrifugation and dispersion in water at pH 9.0 for three-cycles.

Total internal reflectance illuminator microscopy images (TIRFM) of FITC-labeled PVAm nanocapsules were obtained by a fluorescence microscope (Olympus IX71) equipped with a total internal reflectance illuminator. The particles were excited with the 514 nm line of a Coherent Innova 70 Spectrum Kr/Ar laser and images collected with a Q imaging Retiga 1300 CCD. The FITC-conjugated PVAm nanocapsules was then used to visualize the capsule swelling as the pH decreased as set forth in Example 6.

Figure 9:
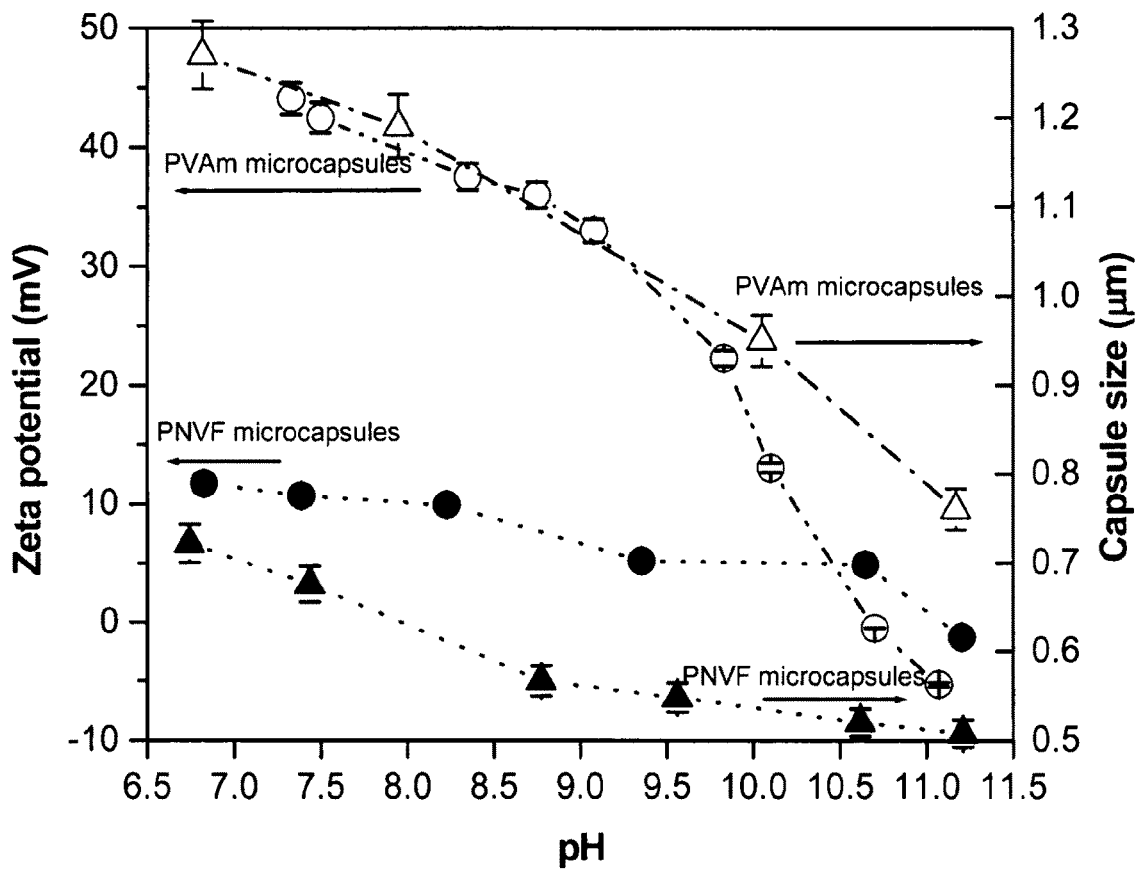
FIG. 9 shows the zeta potential (open circles) and size (open triangles) of PVAm nanocapsules decreased as pH increased. The zeta potential (filled circles) and size (filled triangles) of PNVF nanocapsules (about 30% hydrolyzed) showed similar trends at a lower magnitude.

Next, the zeta potential measurements were employed to evaluate the surface charge of nanocapsules (FIG. 9). For this study, larger capsules were used, which allowed confirmation of the capsule size by total internal fluorescence illuminator microscopy (TIRIF) as well as detection of zeta potential and accurate determination of capsule size by QELS, all with respect to pH. PVAm capsules possessed a positive zeta potential below pH 10.7. The zeta potential increased with decreasing pH, indicating the presence of protonated amino groups as expected. At pH 10.7, the nanocapsules have a zeta potential of about 0 mV because the pKa of PVAm is about 10. Examining the PNVF nanocapsules post-etching but prior conversion to PVAm produced similar trends; however, the magnitude of the change in zeta potential as a function of pH was dampened for the PNVF nanocapsules due to the significant reduction of amino side groups on the capsules (about 30% amino conversion). The observation of comparable, although dampened, zeta potential trends was again attributed to the charged state of the amino side groups on PNVF nanocapsules.

Figure 10:
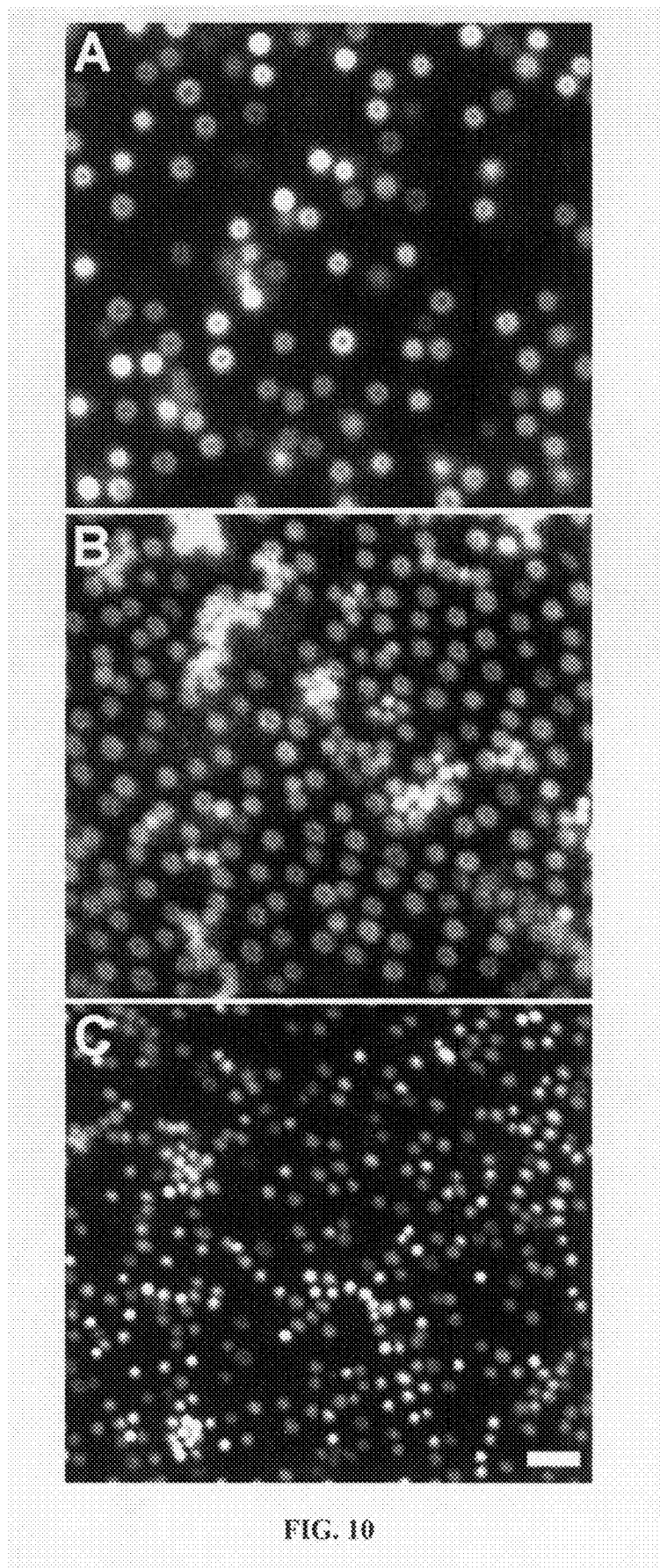
FIG. 10 shows the total internal fluorescence illuminator micrographs of PVAm nanocapsules at a pH of about 11 (panel A), pH of about 7.4 (panel B), and pH of about 6.8 (Panel C).

The diameter of PVAm nanocapsules also exhibited a corresponding pH-dependency. PVAm nanocapsules drastically decreased in diameter with increasing pH (about 1.7 fold diameter change over 4 pH units). The pH dependence of PVAm nanocapsule size correlated extremely well to changes in PVAm protonation (FIG. 9). A similar correlation between zeta potential and nanocapsule size was also observed for PNVF nanocapsules (about 30% hydrolyzed). Total internal fluorescence illuminator micrographs (TIFIM) provided visual evidence that PVAm nanocapsules are hollow and have a larger size at pH 6.8 than at pH 11 (FIG. 10).

As a final examination of these phenomena, PNVF shell/silica core composite nanoparticles with the PNVF shell crosslinked by a non-degradable cross-linker, 2-(N-vinylformamido)ethyl ether, in which the ketal was replaced by an oxygen atom, was produced.

Figure 11:
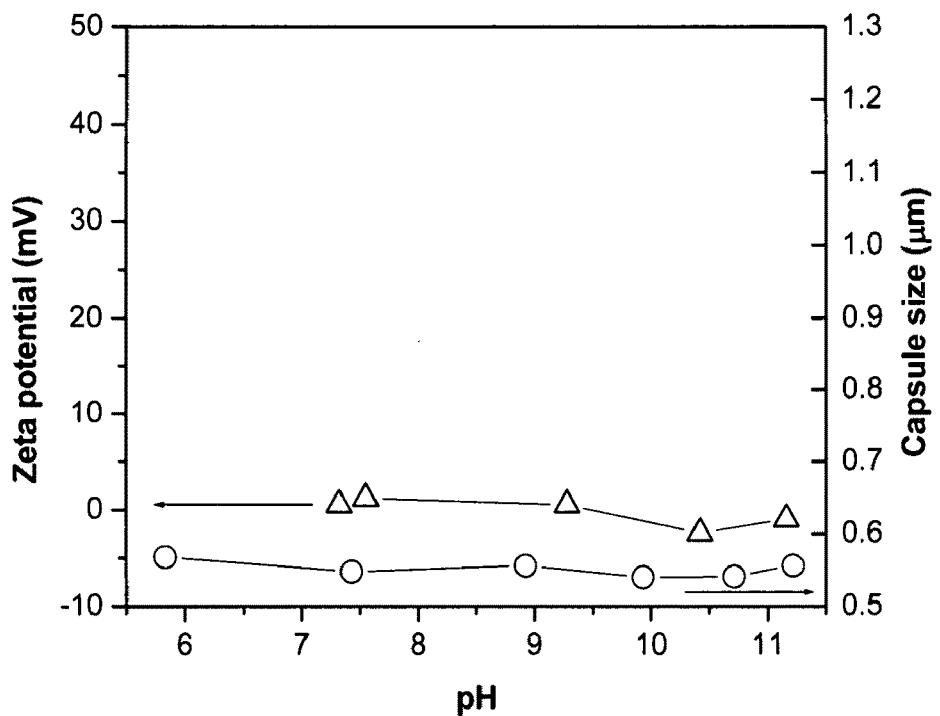
FIG. 11 shows the zeta potential (open triangles) and size (open circles) of PNVF capsules (near 0% amino conversion) as a function of pH. These PNVF capsules were fabricated using a non-degradable cross-linker and by etching silica with HF.
Figure 13A:
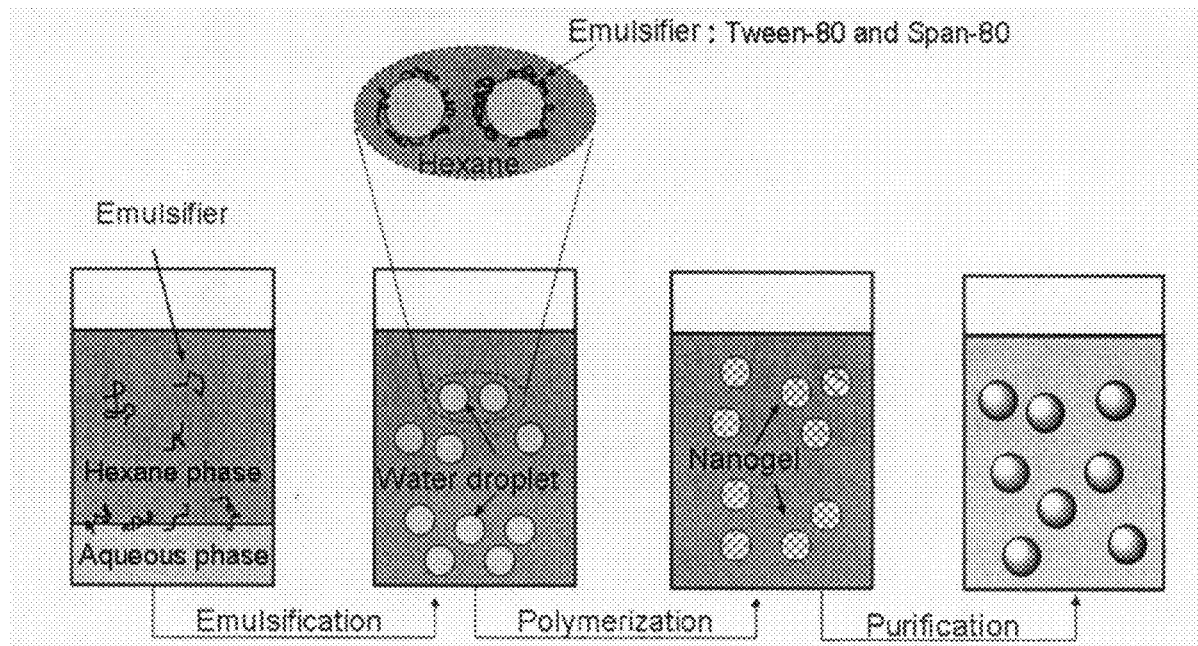
FIGS. 13A and 13B are general schematics showing preparation of the nanogels of the present invention.
Figure 13B:
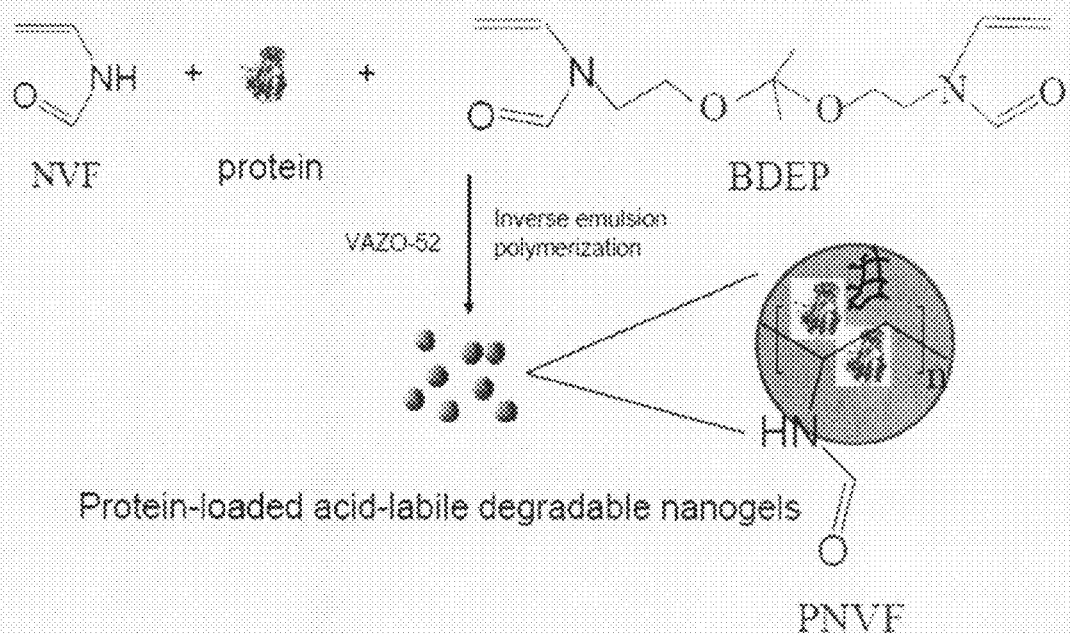

The PNVF nanocapsules were produced with negligible conversion of formamido side groups by etching silica with hydrofluoric acid (HF). These PNVF nanocapsules possessed negligible sensitivity to pH, maintaining a near constant zeta potential (about 0 mV) and size (FIG. 11).

ous phase (optionally in the presence of the active ingredient, e.g., lysozyme) and the initiator. Since polymerization is initiated and contained within water droplets, mainly spherical crosslinked nanoparticles (optionally containing the active ingredient) are produced. The nanoparticles are purified by centrifuging the samples to pellet and isolate the nanoparticles. The particles may be repeatedly resuspended in water or other suitable solvent and centrifuged in order to wash the particles as needed. The synthesis scheme is generally set forth in FIGS. 13A and 13B. The PNVF nanogels had a hydrodynamic diameter of about 100 to 130 nm.

Figure 14:
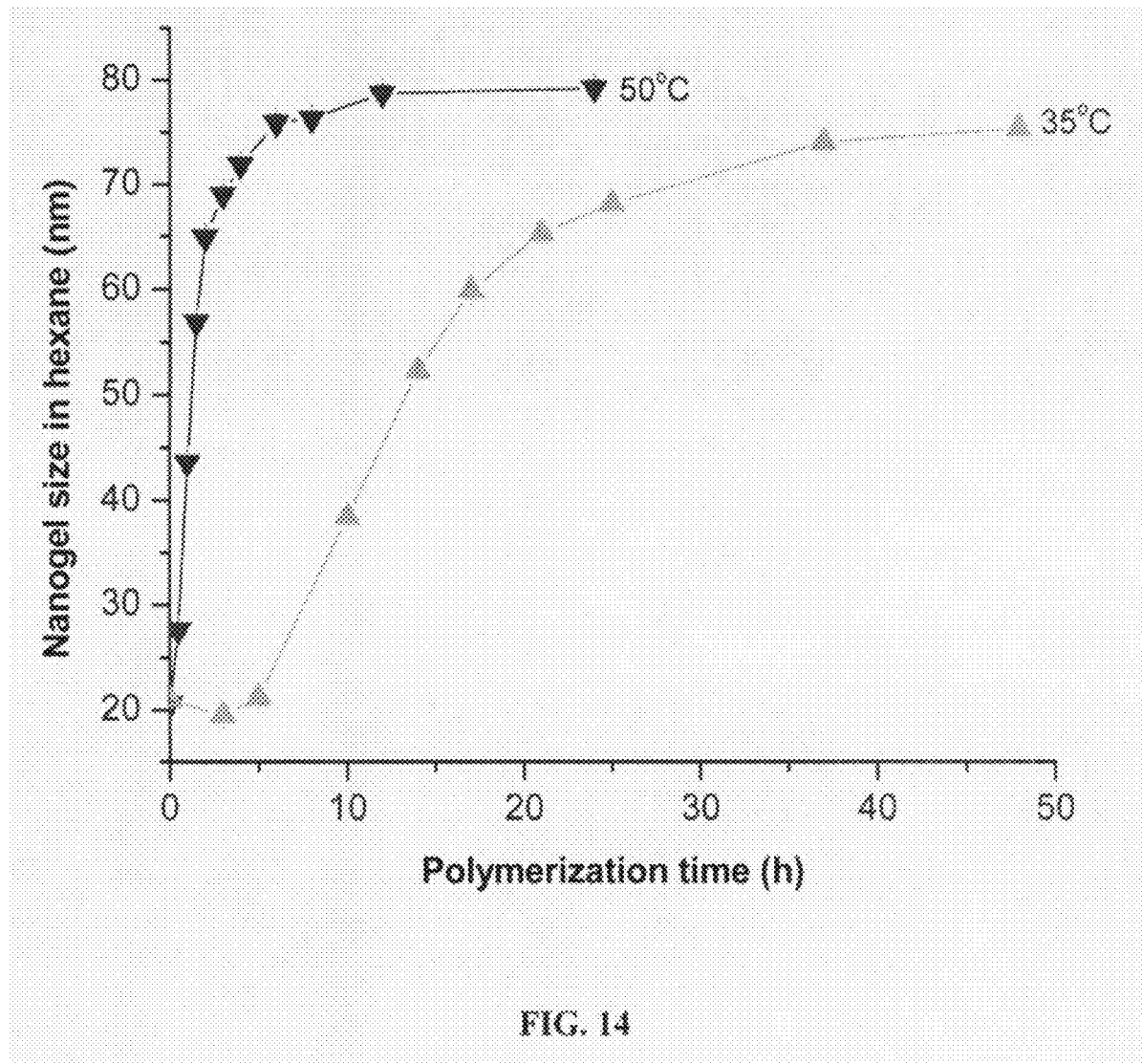
FIG. 14 is a graph illustrating how the PNVF nanogel size may be controlled with polymerization time. Two different polymerization temperatures were investigated (50° C. and 35° C.)

This example was repeated using different polymerization temperatures and times. The results are shown in Table 2 below and FIG. 14.

TABLE 2

Experimental Conditions and Results of PNVF nanogel

| Run$^a$ | NVF (mg) | BDEP (mg) | Nanogel Size in hexane (nm) | Polydispersity | Nanogel size in water (nm) | Polydispersity | Yield of nanogel (%) |
|---|---|---|---|---|---|---|---|
| 1 | 350 | 50 | 79.2 | 0.056 | 137.5 ± 1.3 | 0.128 | / |
| 2 | 350 | 50 | 86.1 | 0.061 | 127.9 ± 1.7 | 0.011 | / |
| 3 | 350 | 50 | / | / | 120.1 ± 2.3 | 0.071 | 98.1 |
| 4$^b$ | 350 | 50 | 74.9 | 0.101 | 104.3 ± 0.5 | 0.158 | 89.3 |

$^a$Run 1,2 and 3: Polymerization temperature: 50° C. Polymerization time: 24 hours
$^b$Polymerization temperature: 35° C. Polymerization time: 48 hours Example 6

Characterization of PNVF Oligomers from Degraded Nanocapsules

In this example, the molecular weight and number of PNVF recovered after nanocapsule degradation was determined by size exclusion chromatography (VE-2001; Viscotek) equipped with a Viscotek 270 dual detector and Viscotek VE3580 RI detector using a GMPW×1 column (column size: 78 mm (ID)×300 mm (L)). An aqueous mobile phase was used consisting of 0.1 M NaNO$_3$ and 0.01% NaN$_3$ at a flow rate of 1.0 mL/min at 35° C.

Figure 12:
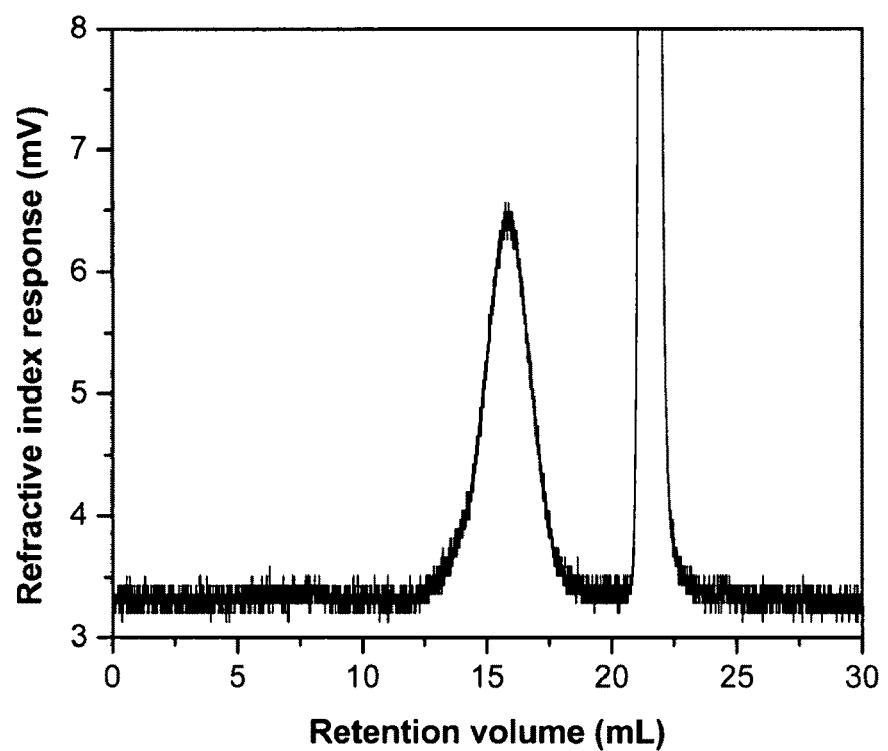
FIG. 12 shows the size exclusion chromatography chromatograph for the PNVF products recovered from degraded nanocapsules.

In order to obtain the molecular weight of products after nanocapsule degradation, PNVF shell/silica core composite nanoparticles crosslinked with BDEP was dissolved in 10% HF. The degraded PNVF was obtained after dialysis of the PNVF solution against water for 24 hours to remove etched silica. FTIR and NMR spectra confirmed that PNVF did not undergo hydrolysis during the dissolution of the particles in 10% HF (data not shown). The molecular weight of the recovered PNVF was 14,800 Da and the molecular weight distribution was 1.45 (FIG. 12).

Example 7A

Preparation of PNVF Nanoparticles Using BDEP

Figure 15:
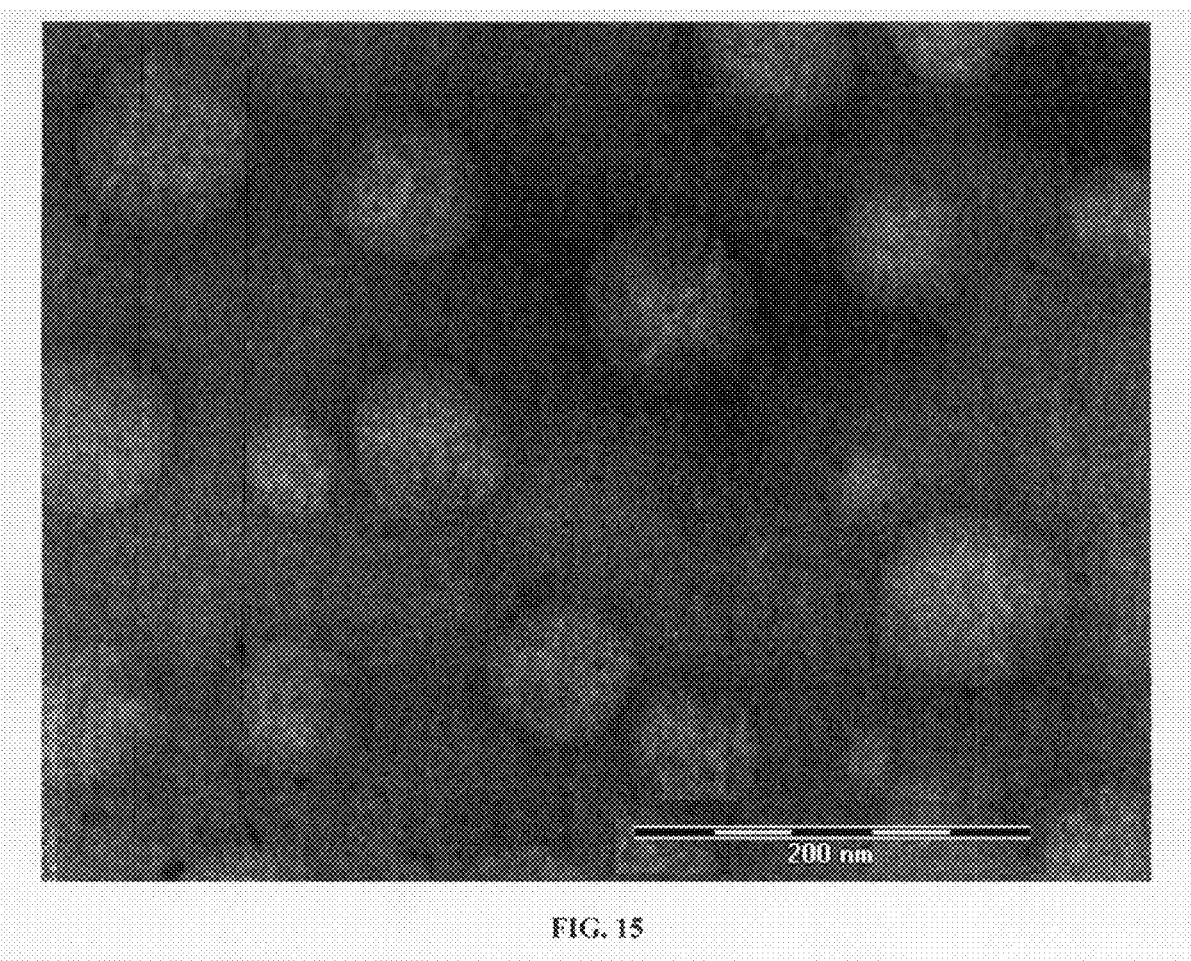
FIG. 15 is a TEM showing an exemplary PNVF nanogel. The nanogels are spherical in size and have a dry particle size of about 70 to 80 nm.

In this example, an acid-labile PNVF nanoparticles were produced. More specifically, the nanoparticles are generally formed by inverse emulsion polymerization using the BDEP as a cross-linker, the azonitrile Vaso-52 (Dupont) as a free radical initiator, PBS buffer (at pH 8.0), and Span 80 (sorbitan monooleate), and Tween 80 (polyethyleneglycol-sorbitan monooleate) as a surfactant at a temperature of about 35° C. During the inverse emulsion polymerization, a small amount of water is dispersed into an organic phase (e.g., hexane) and stabilized by the surfactants. The polymerizable groups and the acid-labile cross-linker are then polymerized in the aque- The PNVF nanogels were then dried by air-drying. The resulting nanogels had a diameter of about 60 to 100 nm, usually around 70-80 nm. A TEM of the dry PNVF nanogels is shown in FIG. 15.

Example 7B

Synthesis of PNVF Nanogel Using NVFEE

A PNVF nanogel was also prepared by inverse emulsion copolymerization of NVF and cross-linker 2-(N-vinylformamido) ethyl ether ("NVFEE") in water droplets, which were dispersed in hexane medium in the presence of surfactant Span-80 and Tween-80. The cross-linker used in this experiment was not acid-labile. However, it was used in this example because it was more easily synthesized than BDEP. However, it is theorized that NVFEE and BDEP may be readily interchanged to form the nanogels, but that BDEP has the additional advantage of being acid-degradable.

Typically, NVF (350 mg), cross-linker (50 mg), and initiator AIBN (20 mg) were dissolved in PBS buffer (160 mg) at pH between 6.5 and 8.5. The solution was emulsified in 100 ml of hexane, which contained AIBN (30 mg), Span-80 (4.1 g) and Tween-80 (3.5 g), under homogenization at about 20,000 rpm for about five minutes. After being purged with nitrogen, the emulsion was heated to about 50° C. and maintained that temperature for about 48 hours. The nanogels were obtained by centrifuge and redispersion in buffer under sonication. The nanoparticle size was about 134±1.3 nm and yield was 89%.

Example 7C

Synthesis of PVAm Nanogel

PNVF nanogel (0.071 g) from Example 7B (using NVFEE) was dispersed in 10 ml of sodium hydroxide aqueous solution (0.1 M) and hydrolysis was carried out at 80° C. for 12 hours. PVAm nanogels were purified by dialysis against nanopure water in dialysis tubing with 2000 MW cut off. The yield was about 54.5%. The conversion of the formamide to amine groups was about 100%.

It will be appreciated that similar PVAm nanogels may be synthesized using acid-labile cross-linkers, such as BDEP. However, because NVFEE is more readily synthesized, it was used in this example.

Example 8

Turbidity Assay of PNVF Nanogels

Figure 16A:
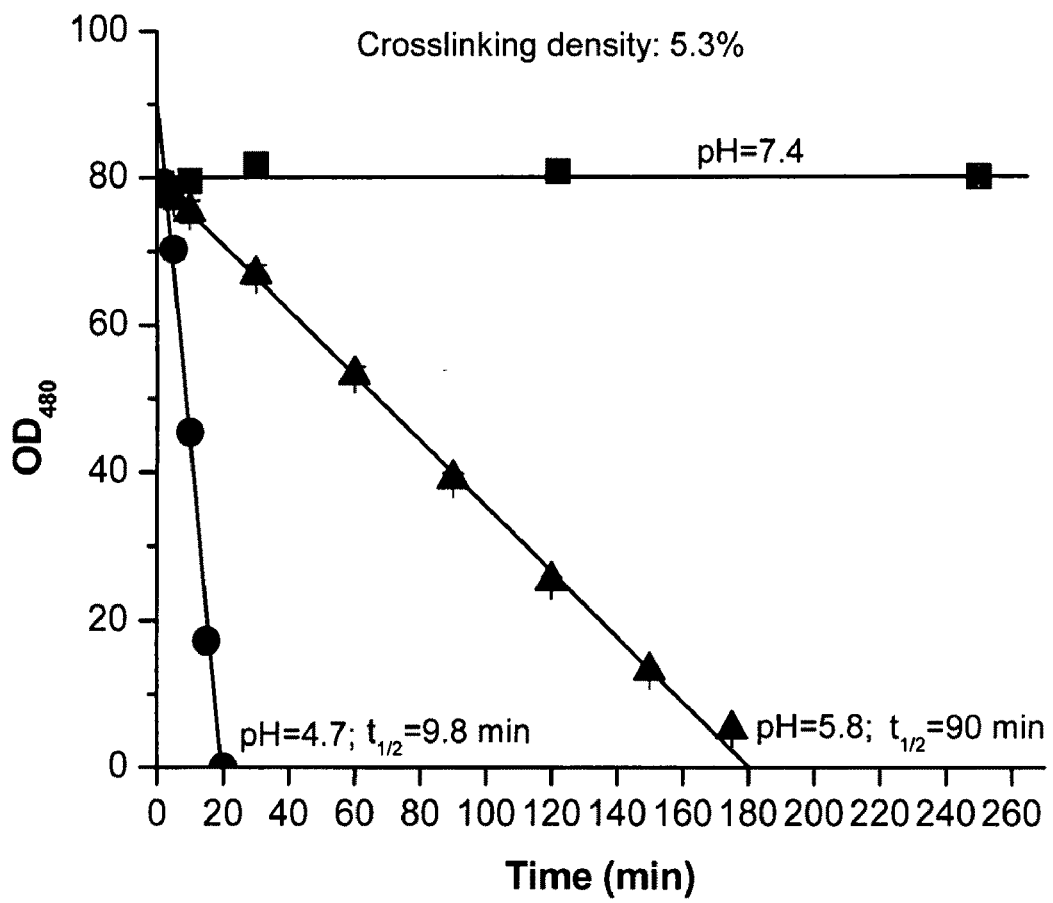
FIGS. 16A and 16B shows the results of a turbidity assay of PNVF nanogels showing the degradation at three different pH values as a function of time (pH of about 7.4, 5.8, and 4.7).
Figure 16B:
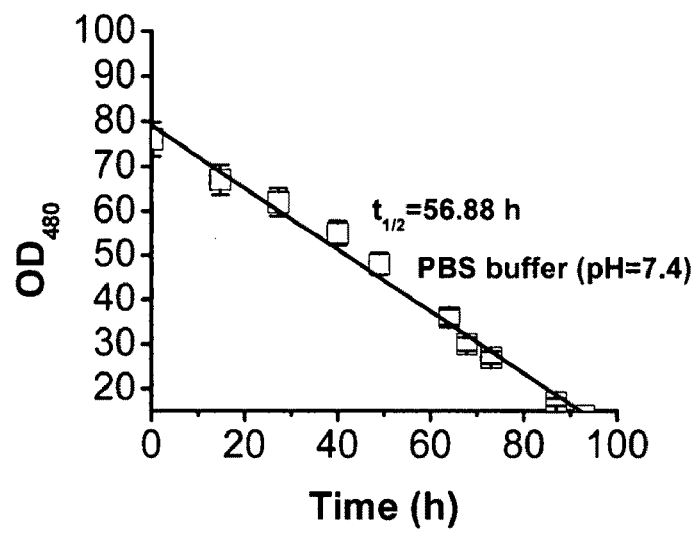

In this example, the degradation of the PNVF nanogels from Example 7A were investigated using a turbidity assay. More specifically, the dispersion kinetics of the nanoparticles were investigated using a 8453 UV/Visible Spectrophotometer (Agilent Technologies), by measuring the optical density at 480 nm at 25° C. at various time intervals. FIG. 16A and FIG. 16B shows that the nanoparticles were relatively stable at a pH of about 7.4. However, when the pH was lowered to about 5.8, the nanoparticles rapidly degraded with a degradation half-life of about 90 minutes. In addition, when the pH was lowered to about 4.7, the degradation rate was even more pronounced. The degradation half-life was about 9.8 minutes when the pH was lowered to 4.7.

Example 9

Encapsulation of Lysozyme in PNVF Nanogels

In this example, nanogels prepared in accordance with Example 7A were also used to encapsulate lysozyme. More specifically, NVF (350 mg), BDEP (50 mg), initiator Vazo-52 (20 mg) and lysozyme (10 mg) were dissolved in PBS buffer (160 mg) at pH 8.0. The solution was emulsified in 100 ml of hexane, which contained Vazo-52 (30 mg), Span-80 (4.1 g) and Tween-80 (3.5 g), under sonication for 30 seconds. After being purged with $N_2$, the emulsion was heated to 35° C. and maintained that temperature for 48 hours. The nanogels were obtained by centrifuge and retispersion in buffer under sonication. The nanogel size was 273±1.7 nm and yield was 49.3%.

Figure 17:
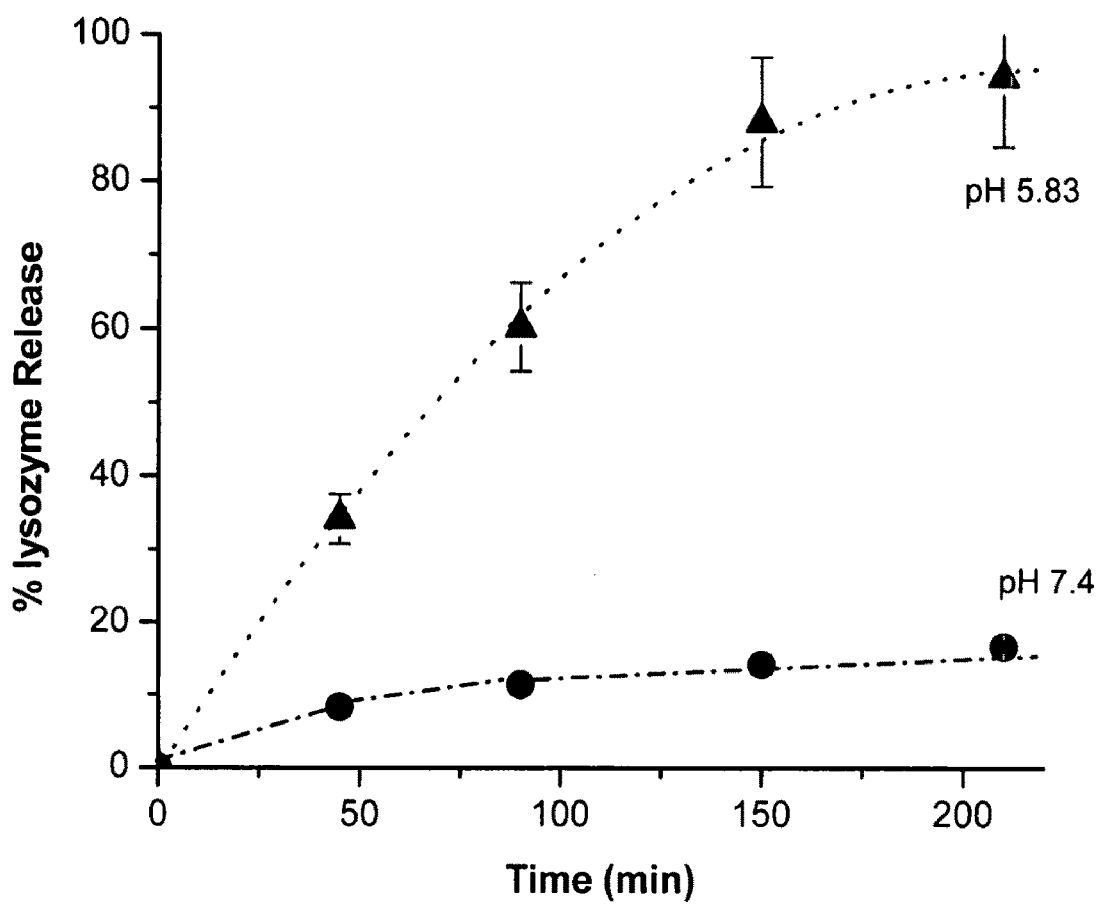
FIG. 17 shows that the PNVF nanogels may be readily degraded by altering the pH, thereby releasing the active ingredient, such as lysozyme.

FIG. 17 also shows the protein (in this case lysozyme) release characteristics as a function of pH. At a pH of 7.4, the nanoparticles remained substantially intact such that less than 20% of the lysozyme was released after 200 minutes. In contrast, when the pH was raised to about 5.8, over 90% of the protein was released in the same amount of time. This example illustrates how the nanoparticles of the present invention may be used for the pH-dependent and controlled delivery of various active ingredients.

Example 10

PVAm Nanogel for Gene Delivery

In this example, PVAm nanogels (about 180 nm) from Example 7C were used to condense DNA for gene delivery applications. The pH of PVAm nanogel suspensions was adjusted to 7.4 with 0.1N HCl and then mixed with different amounts of DNA at room temperature for 20-30 minutes. Stock concentration, then a green fluorescent protein ("GFP") plasmid DNA, used was 0.25 µg/ml in TE buffer (pH 7.4). 600 µl of nanogel suspension was mixed with different volumes of stock DNA ranging from 25 µl to 300 µl. The size of nanogels reduced to 150 nm with 18 mV zeta potential on the addition of 300 µl DNA. Subtracting the amount of DNA in the supernatant of the nanogels from the total DNA added, resulted in 50% binding of DNA to the nanogel in the above mentioned formulation.

Example 11

Preparation of PVAm Nanogel with MRI Agents

In this example, an exemplary MRI agent was conjugated to PVAm nanogels from Example 7C. More specifically Gd-DTPA was conjugated with PVAm nanogels. Gd-DTPA (100.20 mg) was dissolved in 7.5 ml of water and then N-hydroxysuccinimide ("NHS") (22.48 mg) and 1-ethyl-3-(3-dimethyl aminopropyl) carbodiimide hydrochloride ("EDC") (47.76 mg) were added. After the solution was stirred at room temperature for 30 minutes, added 2.5 ml of PVAm suspension, which contained 7.5 mg PVAm nanogel, and adjusted pH to 7.4. The solution was stirred at room temperature for 48 hours. The resultant product was purified by dialysis against nanopure water for 48 hours.

Figure 18:
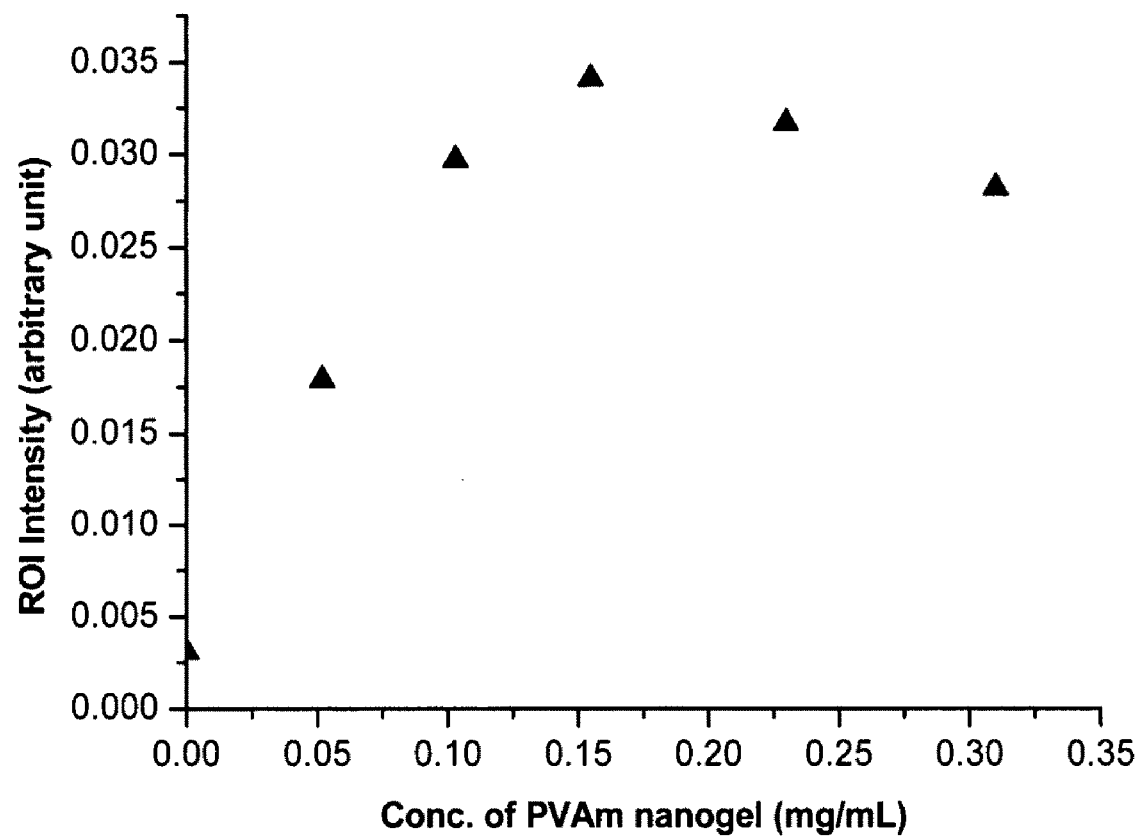
FIG. 18 is a signal intensity curve from a magnetic resonance spectrometer. The concentration at zero mg/ml (zero percent) is the normal signal for water. The use of gadolinium-modified nanogels allows for enhancement of the contrast. Thus, the nanoparticles of the present invention are well-suited as MRI tracers and contrast agents.

FIG. 18 shows the MRI signal vs concentration of Gd-PVAm nanogel. The concentration at zero mg/ml (zero percent) is the normal signal for water. The use of gadolinium-modified nanogels allows for enhancement of the contrast. Thus, this example shows that the nanoparticles of the present invention are well-suited for use in conjunction with MRI tracers and contrast agents.

Example 12

Preparation of PEG-PVAm Nanogel with MRI Agents

In this example, an exemplary MRI agent was conjugated to PVAm nanogels from Example 7C that were also conjugated to polyethylene glycol. First, $PEG_{2000}$ was conjugated onto PVAm nanogels (PEG-PVAm nanogels). PVAm nanogel (10 mg) was dispersed in 5 ml of PBS buffer. After PVAm suspension was adjusted to pH 7.83, $PEG_{2000}$ N-hydroxysuccinimidyl ester (50 mg) was added. The solution was stirred at room temperature for 48 hours. PEG-conjugated PVAm nanogel was purified by dialysis to remove unreacted PEG and other byproducts. The use of PEG is theorized to improve circulation half-life and allow better conjugation of targeting ligands to the terminus of the PEG.

Figure 19:
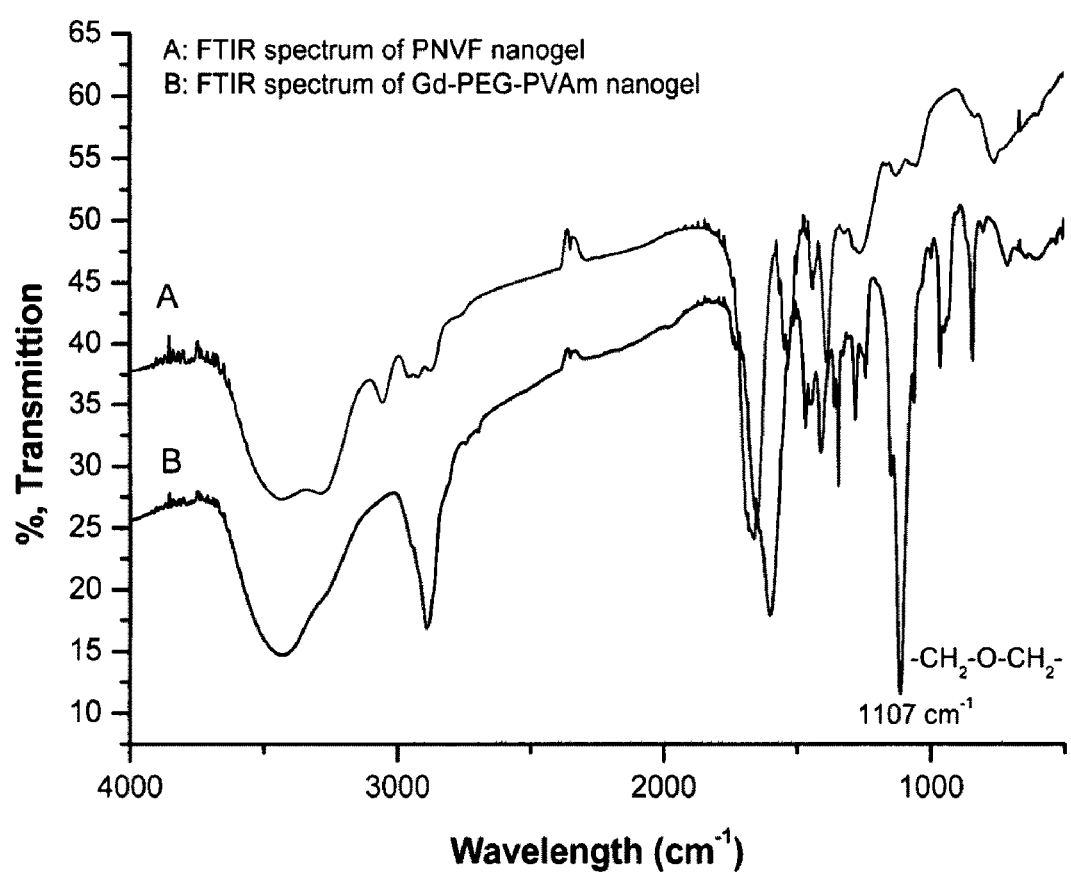
FIG. 19 shows the FTIR spectrum of PNVF nanogels made in accordance with Example 7B, and the FTIR spectrum of the Gd-PEG-PVAm nanogels make in accordance with Example 12.

Next, Gd-DTPA was conjugated with the PEG-PVAm nanogels. More specifically, Gd-DTPA (100.20 mg) was dissolved in 7.5 ml of water and then N-hydroxysuccinimide ("NHS") (22.48 mg) and EDC (74.77 mg) were added. After the solution was stirred at room temperature for 25 minutes, added above PEG-PVAm nanogel suspension and adjusted solution to pH 7.3. The solution was stirred at room temperature for 48 hours. The resulting product was obtained after dialysis against nanopure water for 48 hours. FIG. 19 shows the FTIR spectra of the PNVF nanogels compared to those conjugated with Gd/PEG. The presence of the carboxyl bands in the figure indicates that reaction was successful.

Example 13

Preparation of Small PNVF Nanogels

PNVF nanogels were prepared by inverse microemulsion polymerization. An initiator, VAZO-52, 10 mg was dissolved in 175 µl of vinylformamide. 25 mg of non-degradable cross linker was dissolved in 82.5 µl of water. The cross linker solution was added to the mixture of monomer and initiator.

The organic phase consisted of 50 ml of hexane containing 15 mg of VAZO-52, 5.15 g of Span 80, and 4.5 g of Tween 80. The emulsion was prepared by homogenizing the two phases at 15,000 rpm for 5 minutes at room temperature. The clear solution was stirred under $N_2$ for 20 minutes and then heated to 35° C. for 24 hours. The particle size in hexane was about 13 nm.

Example 14

Preparation of PVAm Nanogels with Magnetite

In this example, PVAm nanogels from Example 7C were conjugated to iron oxide in the form of magnetite (iron oxide), another well-known MRI contrast agent. Further, the use of a magnetic agent permits easy recovery of the nanoparticles or nanocapsules simply by using a magnet.

First, the magnetite nanoparticles were prepared. Fe(II)/Fe(III) solutions were mixed in a molar ratio of 0.5 and at a pH of 11-12. $FeCl_2$ (1.0 g) and of $FeCl_3$ (2.73 g) were dissolved in 0.85 mL of 12.1 N HCl and 25 mL of purified, deoxygenated water with stirring. The combined Fe(II),Fe(III) solution was added drop wise into a 150 mL of 1.5 M NaOH solution. The resulting solution was subjected to strong stirring and a black precipitate formation was observed instantly. The $Fe_3O_4$ black precipitate was isolated by using a magnet and the supernatant was decanted. The precipitate was washed with purified water, with centrifuge at 6000 rpm and decanting the supernatant. This was repeated for three times. The precipitate was dried and obtained as a black powder. The particle size was about 60 nm.

The magnetite was incorporated into the PVAm nanogel from Example 7C having a particle size of about 165-200 nm using by the following method. First, about 500 µL of Solution A was added to about 10 mL solution of PVAm nanogel with vigorous stirring. The light orange solution obtained was allowed to stir overnight, centrifuged at 15,000 rpm for 30 minutes, and the resulted orange precipitate was redispersed in water. To the orange solution, $Fe^{3+}$ solution was added and allowed to stir overnight. (0.2 g of $Fe^{3+}$ was dissolved in 10 mL of 0.1 M NaOH). The resulting dark orange-black solution was centrifuged for 30 minutes at 15,000 rpm to obtain a blackish-orange precipitate. The particle size was about 965 nm.

This procedure was repeated with different concentrations of NaOH, and found that the greenish-black precipitate formation $[Fe(OH)_2]$ is lower in low NaOH concentrations.

Solution A was prepared by dissolving 0.1 g $Fe^{2+}$ in 10 mL of 1.0 M NaOH, a cloudy green solution was resulted upon this.

The references cited herein, as well as the following references, to the extent that they provide exemplary procedural or other details supplementary to those herein, are incorporated herein by reference.

Mathiowitz, E., *Encyclopedia of controlled Drug Delivery*. John Wiley & Sons; Vol. 1 and 2 (1999).

Zhu et al., *Loading of hydrophobic materials into polymer particles: Implications for fluorescent nanosensors and drug delivery*, Journal of the American Chemical Society, 127, (39), 13448-13449 (2005).

Muraoka et al., *Evaluation of intestinal pressure-controlled colon delivery capsule containing caffeine as a model drug in human volunteers*, Journal of Controlled Release, 52, (1-2), 119-129 (1998).

Blackmer et al., Food Chem., (25), 559-561 (1977).

Meier W., *Polymer nanocapsules*, Chemical Society Reviews, 29, (5), 295-303 (2000).

Kozlovskaya et al, *Amphoteric hydrogel capsules: Multiple encapsulation and release routes*, Macromolecules, 39, (18), 6191-6199 (2006).

Koide et al., *Semipermeable polymer vesicle (PICsome) self-assembled in aqueous medium from a pair of oppositely charged block copolymers: Physiologically stable micro-/nanocontainers of water-soluble macromolecules*, Journal of the American Chemical 128, (18), 5988-5989 (2006).

Wong et al., *Assembly of nanoparticles into hollow spheres using block copolypeptides*, Nano Letters, 2, (6), 583-587 (2002).

Sukhorukov et al., *Stepwise polyelectrolyte assembly on particle surfaces: a novel approach to colloid design*, Polymers for Advanced Technologies, 9, (10-11), 759-767 (1998).

Donath et al., *Novel hollow polymer shells by colloid-templated assembly of polyelectrolytes*, Angewandte Chemie-International Edition, 37, (16), 2202-2205 (1998).

Dahne et al., *Fabrication of micro reaction cages with tailored properties*, Journal of the American Chemical Society, 123, (23), 5431-5436 (2001).

Xu et al., *Synthesis and utilization of monodisperse hollow polymeric particles in photonic crystals*, Journal of the American Chemical Society, 126, (25), 7940-7945 (2004).

Tissot et al., *Hybrid latex particles coated with silica*, Macromolecules, 34, (17), 5737-5739 (2001).

Fleming et al., *Nanosphere-microsphere assembly: Methods for core-shell materials preparation*, Chemistry of Materials, 13, (6), 2210-2216 (2001).

Discher et al., *Polymersomes: tough vesicles made from diblock copolymers*, Science 284, (5417), 1143-6 (1999).

Lee et al., *Preparation, stability, and in vitro performance of vesicles made with diblock copolymers*, Biotechnol. Bioeng., 73, (2), 135-45 (2001).

Ahmed et al., *Shrinkage of a rapidly growing tumor by drug-loaded polymersomes: pH-triggered release through copolymer degradation*, Mol Pharm, 3, (3), 340-50 (2006).

Photos et al., *Polymer vesicles in vivo: correlations with PEG molecular weight*, J Control Release, 90, (3), 323-34 (2003).

Li et al., *Synthesis of size-controlled acid-resistant hybrid calcium carbonate microparticles as templates for fabricating "micelles-enhanced" polyelectrolyte capsules by the LBL technique*, Chemistry, 12, (22), 5770-8 (2006).

Khopade et al., *From ultrathin capsules to biaqueous vesicles*, Biomacromolecules, 6, (6), 3433-9 (2005).

Greinacher A., *Heparin-induced thrombocytopenia: frequency and pathogenesis*, Pathophysiol Haemost Thromb, 35, (1-2), 37-45 (2006).

Jones et al., *Polyanions and the proteome*, Mol Cell Proteomics, 3, (8), 746-69 (2004).

Kwon et al., *Morphology of actin assemblies in response to polycation and salts*, Biomacromolecules, 6, (6), 3005-9 (2005).

Forrest et al., *A degradable polyethylenimine derivative with low toxicity for highly efficient gene delivery*, Bioconjug. Chem., 14, (5), 934-40 (2003).

Ma et al., *Microencapsulation of oil with poly(styrene-N,N-dimethylaminoethyl methacrylate) by SPG emulsification technique: effects of conversion and composition of oil phase*, Colloid. Interface Sci., 266, (2), 282-94 (2003).

Beduneau et al., *Pegylated nanocapsules produced by an organic solvent-free method: Evaluation of their stealth properties*, Pharm. Res., 23, (9), 2190-9 (2006).

Scorilas et al., *Polyvinylamine-streptavidin complexes labeled with a europium chelator: A universal detection* reagent for solid-phase time resolved fluorometric applications, Clinical Biochemistry, 33, (5), 345-350 (2000).
Wolfert et al., *Polyelectrolyte vectors for gene delivery: Influence of cationic polymer on biophysical properties of complexes formed with DNA*, Bioconjugate Chemistry, 10, (6), 993-1004 (1999).
Murthy et al., *A macromolecular delivery vehicle for protein-based vaccines: acid-degradable protein-loaded microgels*, Proc. Natl. Acad. Sci. USA, 100, (9), 4995-5000 (2003).
Stöber et al., *Controlled Growth of Monodisperse Silica Spheres in the Micron Size Range*, J. Colloid Interface Sci., 26, 62-69 (1968).
Bourgeat-Lami et al., *Encapsulation of inorganic particles by dispersion polymerization in polar media-1. Silica nanoparticles encapsulated by polystyrene*, Journal of Colloid and Interface Science, 197, (2), 293-308 (1998).
Lorette et al., *Preparation of Ketals from 2,2-Dimethoxypropane*, J. Org. Chem., 25, 521-525 (1960).
Murthy et al., *A novel strategy for encapsulation and release of proteins: Hydrogels and microgels with acid-labile acetal cross-linkers*, Journal of the American Society, 124, (42), 12398-12399 (2002).
Srinivasachar et al., *New Protein Cross-Linking Reagents That Are Cleaved by Mild Acid*, Biochemistry, 28, (6), 2501-2509 (1989).
Ruckenstein et al., *A novel breakable cross-linker and pH-responsive star-shaped and gel polymers*, Macromolecules, 32, (12), 3979-3983 (1999).
Chaimberg et al., *Graft-Polymerization of Polyvinylpyrrolidone onto Silica*, Journal of Applied Polymer Science, 37, (10), 2921-2931 (1989).
Gu et al., *Kinetics and modeling of free radical polymerization of N-vinyl formamide*, Polymer, 42, (7), 3077-3086 (2001).
Uyama et al., *Preparation of Monodisperse Poly(N-Vinyl formamide) Particles by on Polymerization in Methanol Solvent*, Chemistry Letters, (2), 261-262 (1993).
Zha et al., *Monodisperse temperature-sensitive microcontainers*, Advanced Materials, 14, (15), 1090-+(2002).
Gu et al., *Acidic and basic hydrolysis of poly(N-vinyl formamide)*, Journal of Applied Polymer Science, 86, (13), 3412-3419 (2002).
Cordes et al., *Mechanism and catalysis for hydrolysis of acetals, ketals, and ortho esters*, Chemical Reviews, 74, 581-603 (1974).
Kwon et al., *Directed antigen presentation using polymeric microparticulate carriers degradable at lysosomal pH for controlled immune responses*, Molecular pharmaceutics, 2, (1), 83-91 (2005).
Sumaru et al., *Exact evaluation of characteristic protonation of poly(vinylamine) in aqueous solution*, Journal of Physical Chemistry, 100, (21), 9000-9005 (1996).
Kudaibergenov et al., *Swelling, shrinking, deformation, and oscillation of polyampholyte gels based on vinyl 2-aminoethyl ether and sodium acrylate*, Langmuir, 15, (12), 4230-4235 (1999).
Brannon-Peppas et al., *Equilibrium Swelling Behavior of Ph-Sensitive Hydrogels*, Chemical Engineering Science, 46, 715-722 (1991).
Flory P. J., *Principles of Polymer Chemistry*, Cornell University Press: Ithaca, N.Y., p 432-594 (1953).

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or in the accompanying figures are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A composition of matter comprising:
   (a) a nanoparticle template; and
   (b) a polymer shell having an amide side chain formed on said template by polymerizing a monomer with an acid labile cross-linker according to:

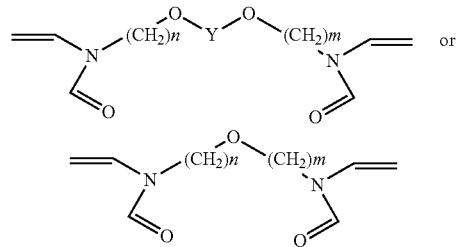

wherein n and m are independently an integer of between 1 and 10; and
   wherein Y is a lower alkyl comprising about 1 to about 6 carbon atoms.

2. The composition of claim 1 further comprising an active ingredient associated with said template or shell.

3. The composition of matter of claim 2, wherein the active ingredient comprises a therapeutic agent or an imaging agent.

4. The composition of matter of claim 3, wherein said active ingredient comprises a peptide, a protein, or a nucleic acid.

5. The composition of matter of claim 1, wherein the nanoparticle template comprises a material selected from the group consisting of silica, ceramic, organic polymer, and combinations thereof.

6. The composition of matter of claim 1, wherein the nanoparticle template comprises a sphere or a rod.

7. The composition of matter of claim 1, wherein the nanoparticle template is a sphere having a diameter ranging from about 1 nanometer to about 1,000 nanometers.

8. The composition of matter of claim 7, wherein the nanoparticle template is a sphere having a diameter ranging from about 5 nanometers to about 500 nanometers.

9. The composition of matter of claim 8, wherein the nanoparticle template is a sphere having a diameter ranging from about 10 nanometers to about 200 nanometers.

10. The composition of matter of claim 1 wherein said shell thickness is between about 20 and 40 nanometers.

11. The composition of matter of claim 1 wherein said polymer shell comprises poly(N-vinyl formamide) ("PNVF") or PNVF that has been partially or fully hydrolyzed to polyvinyl amine ("PVAm").

12. The composition of matter of claim 11 wherein shell comprises PNVF that is about 30 to 50% hydrolyzed to PVAm.

13. The composition of claim 11 wherein said cross-linker is 2-bis[2,2'-di(N-vinylformamido)ethoxy]propane ("BDEP").

14. The composition of claim 11 wherein said cross-linker is 2-(N-vinylformamido)ethyl ether ("NVFEE").

15. The composition of claim 1 wherein said nanoparticle template comprises a silica particle, and said polymer shell formed on said nanoparticle template comprises PNVF or PVAm; and wherein said polymer is cross-linked by an acid labile cross-linker which is BDEP.

16. The composition of matter of claim 15, wherein said shell is hydrolyzed to form a PVAm shell.

17. The composition of matter of claim 1, wherein the shell has a thickness determined by a time of polymerization of the monomer.

18. A method of making the composition of matter of claim 1 comprising:
    forming a suspension of template, monomer, cross-linker, and
    initiator; and polymerizing said monomer onto said template to form a composite nanoparticle.

19. A method for making the composition of matter of claim 18 wherein said method comprises:
    preparing a mixture of N-vinyl formamide monomer ("NVF"), initiator, an acid labile cross-linker in an inverse emulsion where an aqueous phase contains the NVF and the cross-linker, and an aliphatic phase contains a bioactive material;
    emulsifying the mixture to achieve a pre-determined particle size; then
    polymerizing the NVF to form a PNVF nanoparticle.

20. The method of claim 19 wherein said aliphatic phase comprises a lower alkane comprising about 1 to about 6 carbon atoms.

21. The method of claim 19 wherein said mixture further comprises an active ingredient.

22. The method of claim 19 further comprising the step of hydrolyzing said PNVF to form a PVAm nanogel.

* * * * *